(12) United States Patent
Grompe et al.

(10) Patent No.: US 9,566,315 B2
(45) Date of Patent: Feb. 14, 2017

(54) NORMALIZATION OF THE ENTEROHEPATIC CIRCULATION IN ANIMALS WITH A CHIMERIC HUMANIZED LIVER

(71) Applicants: Markus Grompe, Portland, OR (US); Willscott Naugler, Portland, OR (US)

(72) Inventors: Markus Grompe, Portland, OR (US); Willscott Naugler, Portland, OR (US)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 0 days.

(21) Appl. No.: 14/529,011

(22) Filed: Oct. 30, 2014

(65) Prior Publication Data

US 2015/0128299 A1 May 7, 2015

Related U.S. Application Data

(60) Provisional application No. 61/898,793, filed on Nov. 1, 2013.

(51) Int. Cl.
| | | |
|---|---|---|
| A01K 67/00 | (2006.01) | |
| A61K 38/18 | (2006.01) | |
| C12Q 1/68 | (2006.01) | |
| G01N 30/72 | (2006.01) | |
| A01K 67/027 | (2006.01) | |

(52) U.S. Cl.
CPC ....... *A61K 38/1825* (2013.01); *A01K 67/0276* (2013.01); *A01K 67/0278* (2013.01); *C12Q 1/6883* (2013.01); *G01N 30/7233* (2013.01); *A01K 2217/052* (2013.01); *A01K 2217/054* (2013.01); *A01K 2217/15* (2013.01); *A01K 2227/105* (2013.01); *A01K 2267/01* (2013.01); *A01K 2267/0393* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 5,912,173 | A | 6/1999 | Leonard |
| 6,509,514 | B1 | 1/2003 | Kneteman et al. |
| 6,660,905 | B1 | 12/2003 | Kay et al. |
| 8,569,573 | B2 | 10/2013 | Grompe et al. |
| 2005/0255591 | A1 | 11/2005 | Mukaidani |
| 2009/0138976 | A1 | 5/2009 | Charlton |
| 2012/0045764 | A1 | 2/2012 | Grompe |

FOREIGN PATENT DOCUMENTS

| | | |
|---|---|---|
| EP | 1496110 A1 | 1/2005 |
| WO | WO/0017338 A1 | 3/2000 |

OTHER PUBLICATIONS

Clark et al., Nature Reviews: 4: 825-833, 2003.*
Fukumoto et al., Endocrine J. 2008, 55(1)23-31.*
Chiang JY, J Lipid Res 50, 1955-1966 (2009).
Ellis E et al, Hepatology 27, 615-620 (1998).
Chiang JY et al, Gene, 262, 257-265 (2001).
Inagaki T et al, Cell Metab 2, 217-225 (2005).
Lundasen T et al, Intern Med 260, 530-536 (2006).
Katoh M, Int J Mol Med 12, 45-50 (2003).
Dandri et al, Hepatology 33, 981-988 (2001).
Sandgren et al, Cell 66, 245-256 (1991).
Utoh R et al, Am J Pathol 177, 654-665 (2010).
De Vree JM et al, Gastroenterology 119, 1720-1730 (2000).
Guha C et al, Artificial Organs 25, 522-528 (2001).
Weber A et al, Liver Transplantation 15, 7-14 (2009).
Hasegawa M et al, Biochem Biophys Res Commun 405, 405-410 (2011).
Washburn ML et al, Gastroenterology 140, 1334-1344 (2011).
Nishimura T et al, Pharmacol Exp Ther 344, 388-396 (2013).
Nicholes K et al, Am J Pathol 160, 2295-2307 (2002).
Tomlinson E et al, Endocrinology 143, 1741-1747 (2002).
Aponte et al, Proc Natl Acad Sci U S A 98, 641-645 (2001).
Azuma et al, Nature Biotechnol 25, 903-910 (2007).
Bissig et al, Proc Natl Acad Sci U S A 104, 20507-20511 (2007).
Endo and Sun, J Inherit Metab Dis 25, 227-234 (2002).
Grompe et al, Genes Dev 7, 2298-2307 (1993).
Katoh et al, Drug Metab Disposition 32, 1402-1410 (2004).
Katoh et al, Drug Metab Disposition 33, 754-763 (2005).
Katoh et al, Toxicology 246, 9-17 (2007).
Klebig, Proc Natl Acad Sci U S A 89, 1363-1367 (1992).
Mercer et al, Nature Med 7, 927-933 (2001).
Nakamura et al, J Nutrition 137 1556S-1560S (2007).
O'Brien et al, J Virology 47, 649-651 (1983).
Overturf et al, Am J Pathol 155, 2135-2143 (1999).
Shafritz, Nature Biotechnol 25, 871-872 (2007).
Schultz et al, Nat Rev Immunol 7, 118-130 (2007).
Tateno et al, Am J Pathol 165, 901-912 (2004).
Traggiai et al, Science 304, 104-107 (2004).
Turrini et al, Transplant Proc 38, 1181-1184 (2006).
Van Rijn et al, Blood 102, 2522-2531 (2003).
Wang et al, Proc Natl Acad Sci U S A 100, 11881-11888 (2003).
Willenbring et al, Nature Med 10, 744-748 (2004).
Yoshitsugu et al, Drug Metab Pharmacokinet 21, 465-474 (2006).

* cited by examiner

*Primary Examiner* — Doug Schultz
(74) *Attorney, Agent, or Firm* — Jeffrey M. Jackson

(57) ABSTRACT

Methods of normalizing bile acid production in a mouse engrafted with human hepatocytes by the administration of human FGF19 are disclosed. Also disclosed is a transgenic host animal, such as a mouse, that expresses human FGF19 that has normalized bile acid production when engrafted with human hepatocytes.

2 Claims, 10 Drawing Sheets

SEQUENCE LISTING

```
<160> NUMBER OF SEQ ID NOS: 25

<210> SEQ ID NO 1
<211> LENGTH: 216
<212> TYPE: PRT
<213> ORGANISM: Homo Sapiens

<400> SEQUENCE: 1

Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
                20                  25                  30

His Val His Tyr Gly Trp Gly Asp Pro Ile Arg Leu Arg His Leu Tyr
                35                  40                  45

Thr Ser Gly Pro His Gly Leu Ser Ser Cys Phe Leu Arg Ile Arg Ala
            50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
                100                 105                 110

Leu Gln Tyr Ser Glu Glu Asp Cys Ala Phe Glu Glu Glu Ile Arg Pro
            115                 120                 125

Asp Gly Tyr Asn Val Tyr Arg Ser Glu Lys His Arg Leu Pro Val Ser
            130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
                180                 185                 190

Glu Thr Asp Ser Met Asp Pro Phe Gly Leu Val Thr Gly Leu Glu Ala
            195                 200                 205

Val Arg Ser Pro Ser Phe Glu Lys
    210                 215

<210> SEQ ID NO 2
<211> LENGTH: 2157
<212> TYPE: DNA
<213> ORGANISM: Homo sapiens

<400> SEQUENCE: 2
gctcccagcc aagaacctcg gggccgctgc gcggtgggga ggagttcccc gaaacccggc      60
cgctaagcga ggcctcctcc tcccgcagat ccgaacggcc tgggcggggt caccccggct     120
gggacaagaa gccgccgcct gcctgcccgg gcccggggag ggggctgggg ctgggccgg      180
```

```
aggcggggtg tgagtgggtg tgtgcggggg gcggaggctt gatgcaatcc cgataagaaa      240
tgctcgggtg tcttgggcac ctacccgtgg ggcccgtaag gcgctactat ataaggctgc      300
cggcccggag ccgccgcgcc gtcagagcag gagcgctgcg tccaggatct agggccacga      360
ccatcccaac ccggcactca cagccccgca gcgcatcccg gtcgccgccc agcctcccgc      420
acccccatcg ccggagctgc gccgagagcc cagggaggt gccatgcgga gcgggtgtgt       480
ggtggtccac gtatggatcc tggccggcct ctggctggcc gtggccgggc gcccctcgc       540 cttctcggac gcggggcccc acgtgcacta cggctggggc gaccccatcc gcctgcggca      600
cctgtacacc tccggccccc acgggctctc cagctgcttc ctgcgcatcc gtgccgacgg      660
cgtcgtggac tgcgcgcggg gccagagcgc gcacagtttg ctggagatca aggcagtcgc      720
tctgcggacc gtggccatca agggcgtgca cagcgtgcgg tacctctgca tgggcgccga      780
cggcaagatg caggggctgc ttcagtactc ggaggaagac tgtgctttcg aggaggagat      840
ccgcccagat ggctacaatg tgtaccgatc cgagaagcac cgcctcccgg tctcccctgag     900 cagtgccaaa cagcggcagc tgtacaagaa cagaggcttt cttccactct ctcatttcct      960
gcccatgctg cccatggtcc cagaggagcc tgaggacctc aggggccact tggaatctga     1020
catgttctct tcgcccctgg agaccgacag catggaccca tttgggcttg tcaccggact     1080
ggaggccgtg aggagtccca gctttgagaa gtaactgaga ccatgcccgg gcctcttcac     1140
tgctgccagg ggctgtggta cctgcagcgt ggggacgtg cttctacaag aacagtcctg      1200
agtccacgtt ctgtttagct ttaggaagaa acatctagaa gttgtacata ttcagagttt     1260
tccattggca gtgccagttt ctagccaata gacttgtctg atcataacat tgtaagcctg     1320
tagcttgccc agctgctgcc tgggcccccca ttctgctccc tcgaggttgc tggacaagct     1380
gctgcactgt ctcagttctg cttgaatacc tccatcgatg gggaactcac ttcctttgga     1440
aaaattctta tgtcaagctg aaattctcta atttttctc atcacttccc caggagcagc      1500
cagaagacag gcagtagttt taatttcagg aacaggtgat ccactctgta aaacagcagg     1560
taaatttcac tcaaccccat gtgggaattg atctatatct ctacttccag ggaccatttg     1620
cccttcccaa atccctccag gccagaactg actggagcag gcatggccca ccaggcttca     1680
ggagtagggg aagcctggag ccccactcca gccctgggac aacttgagaa ttcccctga     1740 ggccagttct gtcatggatg ctgtcctgag aataacttgc tgtcccggtg tcacctgctt     1800
ccatctccca gcccaccagc cctctgccca cctcacatgc ctccccatgg attggggcct     1860
cccaggcccc ccaccttatg tcaacctgca cttcttgttc aaaaatcagg aaaagaaaag     1920
atttgaagac cccaagtctt gtcaataact tgctgtgtgg aagcagcggg ggaagaccta     1980 gaacccttc cccagcactt ggttttccaa catgatattt atgagtaatt tattttgata      2040
tgtacatctc ttattttctt acattattta tgccccaaa ttatatttat gtatgtaagt      2100
gaggtttgtt ttgtatatta aaatggagtt tgtttgtaaa aaaaaaaaa aaaaaaa         2157
```

<210> SEQ ID NO 3
<211> LENGTH: 6101
<212> TYPE: DNA
<213> ORGANISM: Homo sapiens

<400> SEQUENCE: 3

```
ctcccagcca agaacctcgg ggccgctgcg cggtggggag gagttccccg aaacccggcc        60
gctaagcgag gcctcctcct cccgcagatc cgaacggcct gggcggggtc accccggctg       120
ggacaagaag ccgccgcctg cctgcccggg cccggggagg gggctggggc tggggccgga       180
```

```
ggcggggtgt gagtgggtgt gtgcgggggg cggaggcttg atgcaatccc gataagaaat    240
gctcgggtgt cttgggcacc tacccgtggg gcccgtaagg cgctactata taaggctgcc    300
ggcccggagc cgccgcgccg tcagagcagg agcgctgcgt ccaggatcta gggccacgac    360
catcccaacc cggcactcac agcccgcag cgcatcccgg tcgccgccca gcctcccgca     420
cccccatcgc cggagctgcg ccgagagccc cagggaggtg ccatgcggag cgggtgtgtg    480
gtggtccacg tatggatcct ggccggcctc tggctggccg tggccgggcg ccccctcgcc    540
ttctcggacg cggggcccca cgtgcactac ggctggggcg accccatccg cctgcggcac    600
ctgtacacct ccgccccca cgggctctcc agctgcttcc tgcgcatccg tgccgacggc     660
gtcgtggact gcgcgcgggg ccagagcgcg cacagtgagt gcccgccagc accccgccc    720 gccccgccgc gcgcacccca ccccgctgcg cgcgcccac cccagcgccc ttccttcctt     780
tgccacccTT aggctcctgc ggaccccTCA actcctggga accccaggtt ttggcacctg    840
gacgttagga tccctccgtt agtccccaaa cagcgcggga cgctagggag aagcacaggc    900
ttgtggaccg accgcaccca cgtggtgcgg gccagcggt ccttgctgca gcttctcgct     960
tcccctgcgc ctaggtttgc tggagatcaa ggcagtcgct ctgcggaccg tggccatcaa    1020
gggcgtgcac agcgtgcggt acctctgcat gggcgccgac ggcaagatgc aggggctggt    1080
aagtgtcccc acggggcgga tgcgccgggg cgggggaccg cgcctgtcc ccgggcggag     1140 gcctgaagga gagaaaggcg ctggttcgaa tccagggttt cctcgcctcc tccgcccaga    1200
cccgcgtgca acttcgaggg aaagattgca aagaccgatt aagtgcatgt ccgacgattt    1260
cctacggaaa tttagggtct cagccagcag ccagagaata ggcaaaagct gcctttgcat    1320
ttccaattga gtcaaaggcc ggcctagccg gaccgaggaa acccattatt cggcctcctt    1380
tgatattaaa caggaaaacc cacctcgggc cttttcagcc tctgcctgcg cgtgtgtggt    1440
cctcgcctcc gtttccctcc ctccagtata aagaagaaa aaaagaatgg gaaagaaaaa     1500
agaggatcta cccataactt tccttaaaa acaaatcaat tgtcaagcaa ggcagaaaac     1560
agtgcatttg ggataggaga gattttttt ttagaattaa ttttaatct accaggagca     1620 cggtgtggct tagacgcaga tgcgctggag tcatgttgcg ccaggggagt gcttttcctc    1680
ctgcgggcct cacctgtcct gtaaacgctt tctggtgggg gcaggggtg ggggctggca     1740 gggaaggccc aggtaaccgc agaggtcccg gggccggaag tgtacgagcg ctggggctct    1800
ggtggccggg aacaaaggct gggagttcaa aggaacgaac ccgcgcccct cccgcggccc    1860
cgcgcgcaga ggaggctgtg tgaggtctcg gcccgcgcag gcctcacacg cagccccgga    1920
ctccctggcg gagcaggggc cagggcgggg gtggccgcgc ctgcccgggg cccccacccc    1980
agaaaggatg cagaggcggg gccgcctccg gcccaaccag ctcctttgtg aacagcggga    2040
caaagcattt tagagtctca aaattgctcg gtgcctctgc cgtgctccgt gtactcggag    2100
cgcctgtttc aggttttatg gcggagtcct gcgtgagagg actgcagaga aaggggtgg     2160 tcggcacgct ggacgctgac tcccacccag agccgctcca aacccaccct tgcaacttta    2220
attttgacat ttactatggc aggggtgtg gggggttccta atgatgggag gccagcaggg    2280
gacgtcaacc taacccgcca ttctgcccaa attgggggtt gggtcacctg aaatccctct    2340 gtgcctttt ttttttttt tttttttttt tttggcagag tcttgctctg tcgcccaggc     2400
tggaatgcag tggccagatc tcggctcact gcaacctgtg cctcccaggt tcaagcgttt    2460
ctgctacctc agcctcccat ggagctggga ttacaggtac ccaccaccaa gcccagctac    2520
```

```
cttttgtatt ttgggtagag atggggtttc accatgttgg tggccaggct ggtcttgaac    2580
tcccgacctc aagtgatccg gccgtctcgg cctcccaaag tgctttggga ttagaggtgt    2640
gagccaccgc gcccagcccc ctttgtgcct cttgatcccc tgtgcatggt ctaacagaaa    2700
ttgaggatct tttttttttt tttttttttt ttgagacgga gtctcgcttg ctctgtcgcc    2760
caggctggag tacagtggta tgatcttggc tcactgcaac ctccacctgc ggggttcaag    2820
caattctcct gcctcagcct cccaagtagc tgggattacg gcaccgtgc caccatgacc     2880
ggctagtttt tttgtatttt tagtagagat gaggtttcac catcctggcc aggctggtct    2940
cgaactcctg acatcacgat ctgcctgcct cagccgccca agtgctggga ttacaggca     3000
tgagccacct cgcctggcct ctttcttaaa taaaaatgcc acattcttct agaaacttga    3060
agtcatttcg ttttctgtat ggagaaagtg atactaattt ctcccaaagg acaagccaag    3120
taaatagaag aaggtcctcc aatcattcgg ttttgtgttc cttgtttatt gatcatttgg    3180
cattttgggg agtttgggag aaatcacgct tgctgtccga tgctttgtcc cagccatccg    3240
tgggctcggc aggagcctgg gttgctgcaa tgagcctctt atcaggagct tattagcaca    3300
ggtacctcgt cacccacctg cagttcagtg acctttgcag acttaggcag gaacctgact    3360
gaggccgtcc tgcagtgtgt ttactgccca gcccttccgg ctcccgcctg cgcctgtcct    3420
gggtcgccaa ggggtaatga caccggtgtg ggatggcact tgcccactgg cacctctcaa    3480
ccccgtggac tatgaatgtt ctaagacaag gcttccctca gcacacattt ccggccacca    3540
gctgggcgcc ggcctggcct ggcctggcct gggggagggg ctgctgagat ctgcctcctg    3600
gcagcctgcc tggaaggccc ttggtgactg aatggaggag acagcggggc tgatggttct    3660
cagaactgct gcagaccaga aggccttaga atgataaagg cacacagtga tttctgagat    3720
aggtggggaa cagatgcttt catctgggac ccagatcgga tcacacgcaa tttatttaaa    3780
agacctatcc taagatgaca acccagttta tcagtgtttc ccaaagtgcc aatgaaatac    3840
ccaggaactt tttaaatgcc aggagttatg tctgtaatgt aaagggtgag ggaaacacag    3900
acggcattcc tgtgggttga tggatattat tgcttaggac aaggctctcg aaaaagtgag    3960
gtaatttagt ggaaattatt tgggtctata tagagtgtat atgtagtatt aagtatatac    4020
ataaaatata catatatgaa ataataaacc tcagttttgt ctgtgtgcat gtatatctat    4080
ataaagatta taatttataa aggtatataa atgtatattt aatttattaa tgggttatat    4140
attaacataa tgtacatatt atatatgctt acacttacag tacatttata tatgtgtgtg    4200
tgttctctgt gtatatatat agttgtgggt ttttgtttt gtttttttt gagacagggt      4260
cttgctctat cacccagact agagtgcagt ggcatgatca ttgctcagtg cagccttgac    4320
tacccagcct caacccatcc tcccacctct cagcctcccg aatagctggg cctacaggcg    4380
cccacctcca tgacctgcta atgtttgtac tttttgtcaa gatggaattt taccatgttg    4440
cccaggctgg tctcaaactc ctggattcag gtgatccatc tgctctgggc ctcccaaagt    4500
gctgggacta caggtgtgac ctactgtgcc tggccttaaa gtacattata tattatatat    4560
acttacatat ataaaggtat attttatata tacttacacg tacagtgtgt acatcaggaa    4620
gtatgtataa aacatgcaag tgatgcttat gtggaaggtc actgctggtg gccaccaggg    4680
acagtctgta gcacaaacgt ccatgtggac ccgtgttccc tgtccactgt ggattgctca    4740
gagctgcctg ttttctctgc agcttcagta ctcggaggaa gactgtgctt tcgaggagga    4800
gatccgccca gatggctaca atgtgtaccg atccgagaag caccgcctcc cggtctccct    4860
gagcagtgcc aaacagcggc agctgtacaa gaacagaggc tttcttccac tctctcattt    4920
```

-continued

```
cctgcccatg ctgcccatgg tcccagagga gcctgaggac ctcagggccc acttggaatc    4980
tgacatgttc tcttcgcccc tggagaccga cagcatggac ccatttgggc ttgtcaccgg    5040
actggaggcc gtgaggagtc ccagctttga aagtaactg agaccatgcc cgggcctctt     5100
cactgctgcc aggggctgtg gtacctgcag cgtgggggac gtgcttctac aagaacagtc    5160
ctgagtccac gttctgttta gctttaggaa gaaacatcta aagttgtac atattcagag     5220 ttttccattg gcagtgccag tttctagcca atagacttgt ctgatcataa cattgtaagc    5280
ctgtagcttg cccagctgct gcctgggccc ccattctgct ccctcgaggt tgctggacaa    5340
gctgctgcac tgtctcagtt ctgcttgaat acctccatcg atggggaact cacttccttt    5400
ggaaaaattc ttatgtcaag ctgaaattct ctaattttt ctcatcactt ccccaggagc     5460
agccagaaga caggcagtag tttaatttc aggaacaggt gatccactct gtaaaacagc     5520
aggtaaattt cactcaaccc catgtgggaa ttgatctata tctctacttc cagggaccat    5580
ttgcccttcc caaatccctc caggccagaa ctgactggag caggcatggc ccaccaggct    5640
tcaggagtag gggaagcctg gagccccact ccagccctgg gacaacttga gaattccccc    5700
tgaggccagt tctgtcatgg atgctgtcct gagaataact tgctgtcccg gtgtcacctg    5760
cttccatctc ccagcccacc agccctctgc ccacctcaca tgcctcccca tggattgggg    5820
cctcccaggc cccccacctt atgtcaacct gcacttcttg ttcaaaaatc aggaaaagaa    5880
aagatttgaa gaccccaagt cttgtcaata acttgctgtg tggaagcagc gggggaagac    5940 ctagaacccct ttccccagca cttggttttc caacatgata tttatgagta atttattttg   6000
atatgtacat ctcttatttt cttacattat ttatgccccc aaattatatt tatgtatgta    6060
agtgaggttt gttttgtata ttaaaatgga gtttgtttgt a                        6101
```

<210> SEQ ID NO 4
<211> LENGTH: 282
<212> TYPE: DNA
<213> ORGANISM: Homo sapiens

<400> SEQUENCE: 4

```
agtgagtgcc cgccagcacc cccgcccgcc ccgccgcgcg caccccaccc cgctgcgcgc     60
gccccacccc agcgcccttc cttcctttgc caccccttagg ctcctgcgga cccctcaact   120
cctgggaacc ccaggttttg gcacctggac gttaggatcc ctccgttagt ccccaaacag   180
cgcgggacgc tagggagaag cacaggcttg tggaccgacc gcacccacgt ggtgcgggcc   240
cagcggtcct tgctgcagct tctcgcttcc cctgcgccta gg                      282
```

<210> SEQ ID NO 5
<211> LENGTH: 2400
<212> TYPE: DNA
<213> ORGANISM: Homo sapiens

<400> SEQUENCE: 5

```
ggtaagtgtc cccacggggc ggatgcgccg gggcggggga ccggcgcctg tccccgggcg     60
gaggcctgaa ggagagaaag gcgctggttc gaatccaggg tttcctcgcc tcctccgccc   120 agaccccgcgt gcaacttcga gggaaagatt gcaaagaccg attaagtgca tgtccgacga   180
tttcctacgg aaatttaggg tctcagccag cagccagaga ataggcaaaa gctgcctttg   240
catttccaat tgagtcaaag gccggcctag ccggaccgag gaaacccatt attcggcctc   300
ctttgatatt aaacaggaaa acccacctcg ggccttttca gcctctgcct gcgcgtgtgt    360
```

| | |
|---|---|
| ggtcctcgcc tccgtttccc tccctccagt ataaagaag aaaaaagaa tgggaaagaa | 420 |
| aaaagaggat ctacccataa ctttccttta aaaacaaatc aattgtcaag caaggcagaa | 480 |
| aacagtgcat ttgggatagg agagattttt ttttagaat taattttaa tctaccagga | 540 |
| gcacggtgtg gcttagacgc agatgcgctg gagtcatgtt gcgccagggg agtgcttttc | 600 |
| ctcctgcggg cctcacctgt cctgtaaacg ctttctggtg ggggcagggg gtggggctg | 660 |
| gcagggaagg cccaggtaac cgcagaggtc ccggggccgg aagtgtacga gcgctggggc | 720 |
| tctggtggcc gggaacaaag gctgggagtt caaaggaacg aacccgcgcc cctcccgcgg | 780 |
| ccccgcgcgc agaggaggct gtgtgaggtc tcggcccgcg caggcctcac acgcagcccc | 840 |
| ggactccctg gcggagcagg ggccagggcg ggggtggccg cgcctgcccg ggcccccac | 900 |
| cccagaaagg atgcagaggc ggggccgcct ccggcccaac cagctccttt gtgaacagcg | 960 |
| ggacaaagca ttttagagtc tcaaaattgc tcggtgcctc tgccgtgctc cgtgtactcg | 1020 |
| gagcgcctgt ttcaggtttt atggcggagt cctgcgtgag aggactgcag agaaaggggg | 1080 |
| tggtcggcac gctggacgct gactcccacc cagagccgct ccaaacccac ccttgcaact | 1140 |
| ttaattttga catttactat ggcaggggt gtggggttc ctaatgatgg gaggccagca | 1200 |
| ggggacgtca acctaacccg ccattctgcc caaattgggg gttgggtcac ctgaaatccc | 1260 |
| tctgtgcctt tttttttttt tttttttttt tttttggca gagtcttgct ctgtcgccca | 1320 |
| ggctggaatg cagtggccag atctcggctc actgcaacct gtgcctccca ggttcaagcg | 1380 |
| tttctgctac ctcagcctcc catggagctg ggattacagg tacccaccac caagcccagc | 1440 |
| tacctttgt attttgggta gagatggggt ttcaccatgt tggtggccag gctggtcttg | 1500 |
| aactcccgac ctcaagtgat ccggccgtct cggcctccca aagtgctttg ggattagagg | 1560 |
| tgtgagccac cgcgcccagc ccccttgtg cctcttgatc ccctgtgcat ggtctaacag | 1620 |
| aaattgagga tctttttttt tttttttttt ttttgagac ggagtctcgc ttgctctgtc | 1680 |
| gcccaggctg gagtacagtg gtatgatctt ggctcactgc aacctccacc tgcggggttc | 1740 |
| aagcaattct cctgcctcag cctcccaagt agctgggatt acgggcaccg tgccaccatg | 1800 |
| accggctagt tttttgtat ttttagtaga gatgaggttt caccatcctg gccaggctgg | 1860 |
| tctcgaactc ctgacatcac gatctgcctg cctcagccgc ccaaagtgct gggattacag | 1920 |
| gcatgagcca cctcgcctgg cctctttctt aaataaaaat gccacattct tctagaaact | 1980 |
| tgaagtcatt tcgttttctg tatggagaaa gtgatactaa tttctcccaa aggacaagcc | 2040 |
| aagtaaatag aagaaggtcc tccaatcatt cggttttgtg ttccttgttt attgatcatt | 2100 |
| tggcattttt gggagtttgg gagaaatcac gcttgctgtc cgatgctttg tcccagccat | 2160 |
| ccgtgggctc ggcaggagcc tgggttgctg caatgagcct cttatcagga gcttattagc | 2220 |
| acaggtacct cgtcacccac ctgcagttca gtgacctttg cagacttagg caggaacctg | 2280 |
| actgaggccg tcctgcagtg tgtttactgc ccagcccttc cggctcccgc ctgcgcctgt | 2340 |
| cctgggtcgc caagggtaa tgacaccggt gtgggatggc acttgcccac tggcacctct | 2400 |

<210> SEQ ID NO 6
<211> LENGTH: 21
<212> TYPE: DNA
<213> ORGANISM: Artificial Sequence
<220> FEATURE:
<223> OTHER INFORMATION: PCR primer

<400> SEQUENCE: 6
ccaaacagcg cgggacgcta g                                       21

<210> SEQ ID NO 7
<211> LENGTH: 22
<212> TYPE: DNA
<213> ORGANISM: Artificial Sequence
<220> FEATURE:
<223> OTHER INFORMATION: PCR primer

<400> SEQUENCE: 7
aaggcccgag gtgggttttc ct                                          22

<210> SEQ ID NO 8
<211> LENGTH: 19
<212> TYPE: DNA
<213> ORGANISM: Artificial Sequence
<220> FEATURE:
<223> OTHER INFORMATION: PCR primer

<400> SEQUENCE: 8
tcctcccgtg gacggtgct                                              19

<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9
aggcatggcc caccaggctt                                             20

<210> SEQ ID NO 10
<211> LENGTH: 24
<212> TYPE: DNA
<213> ORGANISM: Artificial Sequence
<220> FEATURE:
<223> OTHER INFORMATION: PCR primer

<400> SEQUENCE: 10
tttggggcca caattcagtc actt                                        24

<210> SEQ ID NO 11
<211> LENGTH: 22
<212> TYPE: DNA
<213> ORGANISM: Artificial Sequence
<220> FEATURE:
<223> OTHER INFORMATION: PCR primer

<400> SEQUENCE: 11
tgcctgcttg atctcccttg cc                                          22

<210> SEQ ID NO 12
<211> LENGTH: 21
<212> TYPE: DNA
<213> ORGANISM: Artificial Sequence
<220> FEATURE:
<223> OTHER INFORMATION: PCR primer

<400> SEQUENCE: 12
gtgtttgggg cagcagggga c                                           21

<210> SEQ ID NO 13
<211> LENGTH: 21
<212> TYPE: DNA
<213> ORGANISM: Artificial Sequence
<220> FEATURE:

```
<223> OTHER INFORMATION: PCR primer

<400> SEQUENCE: 13
agctgccacc ggatactggc a                                             21

<210> SEQ ID NO 14
<211> LENGTH: 22
<212> TYPE: DNA
<213> ORGANISM: Artificial Sequence
<220> FEATURE:
<223> OTHER INFORMATION: PCR primer

<400> SEQUENCE: 14
gtgatcttct tgctggtctt gc                                            22

<210> SEQ ID NO 15
<211> LENGTH: 22
<212> TYPE: DNA
<213> ORGANISM: Artificial Sequence
<220> FEATURE:
<223> OTHER INFORMATION: PCR primer

<400> SEQUENCE: 15
gtaagatacg gagggcgcac ag                                            22

<210> SEQ ID NO 16
<211> LENGTH: 24
<212> TYPE: DNA
<213> ORGANISM: Artificial Sequence
<220> FEATURE:
<223> OTHER INFORMATION: PCR primer

<400> SEQUENCE: 16
taggaaccca gaagcaatga aagc                                          24

<210> SEQ ID NO 17
<211> LENGTH: 26
<212> TYPE: DNA
<213> ORGANISM: Artificial Sequence
<220> FEATURE:
<223> OTHER INFORMATION: PCR primer

<400> SEQUENCE: 17
ggatgttgag ggaggcactg gaaagc                                        26

<210> SEQ ID NO 18
<211> LENGTH: 20
<212> TYPE: DNA
<213> ORGANISM: Artificial Sequence
<220> FEATURE:
<223> OTHER INFORMATION: PCR primer

<400> SEQUENCE: 18
cgtcccgtag acaaaatggt                                               20

<210> SEQ ID NO 19
<211> LENGTH: 20
<212> TYPE: DNA
<213> ORGANISM: Artificial Sequence
<220> FEATURE:
<223> OTHER INFORMATION: PCR primer

<400> SEQUENCE: 19
ttgatggcaa caatctccac                                               20
```

```
<210> SEQ ID NO 20
<211> LENGTH: 20
<212> TYPE: DNA
<213> ORGANISM: Artificial Sequence
<220> FEATURE:
<223> OTHER INFORMATION: PCR primer

<400> SEQUENCE: 20
gtgcatctta ggcagctcag                                              20

<210> SEQ ID NO 21
<211> LENGTH: 20
<212> TYPE: DNA
<213> ORGANISM: Artificial Sequence
<220> FEATURE:
<223> OTHER INFORMATION: PCR primer

<400> SEQUENCE: 21
ttcacaaaca cctcccttc                                               20

<210> SEQ ID NO 22
<211> LENGTH: 20
<212> TYPE: DNA
<213> ORGANISM: Artificial Sequence
<220> FEATURE:
<223> OTHER INFORMATION: PCR primer

<400> SEQUENCE: 22
cactggtcat ggctgagaaa                                              20

<210> SEQ ID NO 23
<211> LENGTH: 20
<212> TYPE: DNA
<213> ORGANISM: Artificial Sequence
<220> FEATURE:
<223> OTHER INFORMATION: PCR primer

<400> SEQUENCE: 23
tccgaggaga acaagctgtc                                              20

<210> SEQ ID NO 24
<211> LENGTH: 20
<212> TYPE: DNA
<213> ORGANISM: Artificial Sequence
<220> FEATURE:
<223> OTHER INFORMATION: PCR primer

<400> SEQUENCE: 24
aagggcacga tcctcttcaa                                              20

<210> SEQ ID NO 25
<211> LENGTH: 20
<212> TYPE: DNA
<213> ORGANISM: Artificial Sequence
<220> FEATURE:
<223> OTHER INFORMATION: PCR primer

<400> SEQUENCE: 25
ctgttgcagg tgtgcgatgt                                              20
```

NORMALIZATION OF THE ENTEROHEPATIC CIRCULATION IN ANIMALS WITH A CHIMERIC HUMANIZED LIVER

ACKNOWLEDGEMENT OF GOVERNMENT SUPPORT

This invention was made with United States government support under the terms of grant number R01DK05192 awarded by the National Institutes of Health. The United States government has certain rights in the invention.

FIELD

This disclosure relates to the use of animals engrafted with human hepatocytes and specifically to the normalization of human hepatocyte activity in said animals by providing them with human FGF19.

BACKGROUND

The use of experimental animals in scientific research has enabled some of the most important breakthroughs in medical research (*The use of non-human animals in research: a guide for scientists*: The Royal Society, 2004, incorporated by reference herein). Further refinement of animal models through genetic manipulation is an important and powerful tool in research today. By transplanting human cells and tissues into genetically engineered mice these possibilities are taken to a new level. Humanized mouse models present opportunities to study whole cellular systems in an in vivo setting (Strom S C et al, *Methods Mol Biol* 640, 491-509 (2010); Kamimura H et al, *Drug Metab Pharmacokinet* 25, 223-235 (2010); Schultz L D et al, *Nat Rev Immunol* 7, 118-130, (2007); Katoh M et al, *Toxicology* 246, 9-17 (2008) all of which are incorporated by reference herein). One such humanized mouse model is a mouse engrafted with human hepatocytes.

SUMMARY

Several mouse models can support transplantation of human hepatocytes through subsequent repopulation of the mouse liver with human hepatocytes, thus "humanizing" the mouse liver. Such mice with humanized livers are valuable tools for (1) studying human liver diseases to which mice are otherwise not susceptible, (2) studying drug metabolism in a model system that more closely resembles the human condition, and (3) growth and expansion of human hepatocytes which cannot otherwise be expanded in vitro for potential therapeutic use in human diseases. Examples of uses of mice engrafted with human hepatocytes and hepatocytes expanded in mice are discussed in Grompe et al., WO 2008/151283 (December 2008) and Grompe and Lan, WO 2010/127275 (November 2010), both of which are incorporated by reference herein.

While most functions of the liver are normal in mice with humanized livers, the bile acid profile is perturbed. Specific abnormalities observed in mice with humanized livers are: (1) bile acid species are markedly different than either normal human or normal mouse, most clearly demonstrated by the percentage of unconjugated bile acids seen in the bile of these mice (about 15%) compared to normal mice or humans (<1%); (2) bile acid synthesis is highly upregulated as demonstrated by the marked upregulation of the rate-limiting enzyme controlling bile acid synthesis (Cyp7a1); and (3) the total (entire body) bile acid pool is 2 to 3 times the size that of normal mice. It is disclosed herein that providing human FGF19 to mice engrafted with human hepatocytes normalizes bile acid synthesis and growth responses of the human hepatocytes.

One embodiment encompasses a method of normalizing bile acid production in a mouse engrafted with human hepatocytes. In this embodiment, the FGF19 may be provided exogenously through the administration of a composition that comprises an effective amount of human FGF19 to the mouse. In examples of this embodiment, the mouse may be immunodeficient and/or deficient in expression of the Fah gene. The method may further comprise detecting an outcome of normalizing bile acid production. Such outcomes may include lower liver weight, lower bile acid concentration, CYPA7 expression similar to that of normal human hepatocytes, or any combination of these in FGF19 treated animals relative to non FGF19 treated animals.

Another embodiment encompasses a transgenic mouse that has a disruption in one or more genes that renders the mouse deficient in the expression of FAH protein, a disruption in one or more genes that renders the mouse immunodeficient, and a nucleic acid construct that comprises a nucleic acid sequence that encodes human FGF19. The disruption that renders the mouse deficient in the expression of FAH may be any disruption or combination of disruptions including a homozygous disruption in the Fah gene. The disruption that renders the mouse immunodeficient can be any such disruption including a disruption in the Rag1 gene, the Rag2 gene, or a combination of the two. However, any disruption that renders the mouse immunodeficient may be used. Examples include a SCID mutation, a nude mouse mutation, or any disruption that results in a non-obese diabetic (NOD) phenotype.

The foregoing and other objects, features, and advantages of the disclosure will become more apparent from the following detailed description, which proceeds with reference to the accompanying figures.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is the sequence of human FGF19 protein.
SEQ ID NO: 2 is the sequence of human FGF19 cDNA
SEQ ID NO: 3 is the sequence of genomic human FGF19 DNA/unspliced RNA
SEQ ID NO: 4 is the sequence of human FGF19 intron 1
SEQ ID NO: 5 is the sequence of human FGF19 intron 2.
SEQ ID NO: 6 is the sequence of a forward primer that amplifies the P1 region of BAC RP11-266K14 indicated in FIG. 11.
SEQ ID NO: 7 is the sequence of a reverse primer that amplifies the P1 region of BAC RP11-266K14 indicated in FIG. 11.

Figure 11:
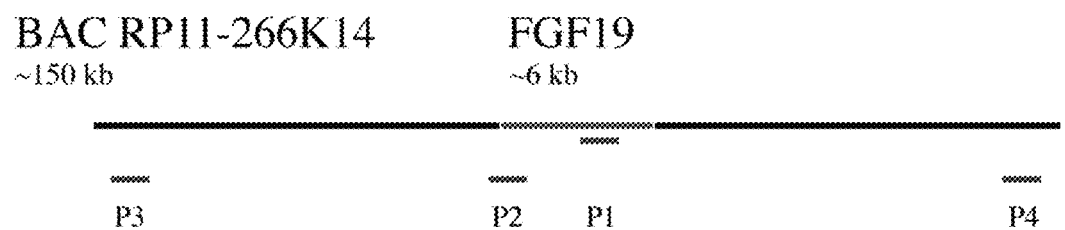
FIG. 11 is a map of the BAC RP11-266K14 construct used to generate the transgenic mice described herein. The (lighter) center portion is the 6 kb genomic sequence of the human FGF19 gene. The areas indicated P1, P2, P3, and P4 are locations that are amplified using specific PCR primers to detect the presence of intact FGF19 and/or the BAC construct.

SEQ ID NO: 8 is the sequence of a forward primer that amplifies the P2 region of BAC RP11-266K14 indicated in FIG. 11.

SEQ ID NO: 9 is the sequence of a reverse primer that amplifies the P2 region of BAC RP11-266K14 indicated in FIG. 11.

SEQ ID NO: 10 is the sequence of a forward primer that amplifies the P3 region of BAC RP11-266K14 indicated in FIG. 11.

SEQ ID NO: 11 is the sequence of a reverse primer that amplifies the P3 region of BAC RP11-266K14 indicated in FIG. 11.

SEQ ID NO: 12 is the sequence of a forward primer that amplifies the P4 region of BAC RP11-266K14 indicated in FIG. 11.

SEQ ID NO: 13 is the sequence of a reverse primer that amplifies the P4 region of BAC RP11-266K14 indicated in FIG. 11.

SEQ ID NO: 14 is the sequence of a murine cyclophilin forward primer.

SEQ ID NO: 15 is the sequence of a murine cyclophilin reverse primer.

SEQ ID NO: 16 is the sequence of a murine CYP7A1 forward primer.

SEQ ID NO: 17 is the sequence of a murine CYP7A1 reverse primer.

SEQ ID NO: 18 is the sequence of a murine GADPH forward primer.

SEQ ID NO: 19 is the sequence of a murine GADPH reverse primer.

SEQ ID NO: 20 is the sequence of a murine ABCG5 forward primer.

SEQ ID NO: 21 is the sequence of a murine ABCG5 reverse primer.

SEQ ID NO: 22 is the sequence of a murine ABCG8 forward primer.

SEQ ID NO: 23 is the sequence of a murine ABCG8 reverse primer.

SEQ ID NO: 24 is the sequence of a murine SHP forward primer.

SEQ ID NO: 25 is the sequence of a murine SHP reverse primer.

DETAILED DESCRIPTION

I. Introduction

Rodents and humans have marked differences in their bile acid profiles. This disclosure shows that FRG mice that have been engrafted with human hepatocytes (also referred to as "engrafted mice" or "humanized mice") have bile acid profiles that are significantly different than those of humans. Humans can amidate bile acids with both glycine and taurine (Sjovall J, *Proc Soc Exp Biol Med* 100, 676-678 (1959), incorporated by reference herein) with a preference for glycine in adulthood. Mice conjugate almost exclusively with taurine (Inoue Y et al, *J Biol Chem* 279, 2480-2489 (2004), incorporated by reference herein). The disclosure and the Examples below demonstrate that engrafted mice conjugate bile acids with glycine.

Yet another difference between mice and humans is bile acid composition. It is disclosed in the Examples below that the percentage of β-muricholic acid (BMCA) is lower in engrafted mice relative to control non-engrafted FRG mice. Deoxycholic acid (DCA) and the ratio of DCA/BMCA was significantly higher in both highly and moderately engrafted mice relative to control non-engrafted FRG mice. These characteristics are not reflective of a normal human bile acid profile.

An additional difference in the bile acid profile between mice and humans is a higher synthesis rate of bile acids. Normal humans synthesize about 500 mg of bile per day which corresponds to about 0.35 mg per gram of liver (Einarsson K et al, *N Engl J Med* 313, 277-282 (1985), incorporated by reference herein). Mice synthesize 4.3 mg per day per 100 grams of body weight, which corresponds to about 0.78 mg of bile per day per gram of liver (Yokoyama H O et al, *Cancer Res* 13, 80-85 (1953) and Schwarz M et al, *J Lipid Res* 39, 1833-1843 (1998), both of which are incorporated by reference herein.) Therefore, mice synthesize bile acids at double the rate of humans. It is disclosed in the Examples below that engrafted mice also synthesize bile acids at a high rate more reflective of the bile acid synthesis rate of mice rather than the bile acid synthesis rate in humans.

One more difference in the bile acid profile between mice and humans is the ability of rodent hepatocytes to rapidly transform CDCA, DCA and CA into β-muricholic acid (Princen H M et al, *Biochem Biophys Res Commun* 154, 1114-1121 (1988), incorporated by reference herein.) Muricholic acids are not present in human bile. The β-muricholic acid form is the most prevalent muricholic acid present in mouse bile. It is well known that the different bile acids regulate overall bile acid synthesis differently in different species (Ellis E et al, *Hepatology* 38, 930-938 (2003), incorporated by reference herein).

As is disclosed herein, bile acid abnormalities observed in mice with humanized are due to abnormal signaling between the intestine and the liver. In normal homeostasis, the liver synthesizes bile acids, excretes them from hepatocytes into the bile via a specific transporter (BSEP) where they eventually enter the lumen of the intestine, there to aid in the digestion and absorption of fats. At the end of the small intestine, these bile acids are efficiently taken up into the enterocytes via specific receptors (ABST), transported into the portal blood where they return to the liver and are taken up by specific receptors (NTCP) into the hepatocyte. This circuit of bile acids describes an enterohepatic circulation (EHC), and occurs 4-6 times per day in both humans and mice. Despite the highly dynamic EHC, the total bile acid pool remains static, as a small amount (about 5%) is lost in the feces daily, made up for by de novo synthesis in the liver (for review see Chiang J Y, *J Lipid Res* 50, 1955-1966 (2009) incorporated by reference herein.) The size of the bile acid pool is controlled by a negative feedback loop between the small intestine enterocyte and the hepatocyte. When an excess of bile acids is present, the small intestine enterocyte produces a signaling molecule called Fibroblast Growth Factor 15 (FGF15) in the mouse. FGF15 travels to the liver where it engages its cognate receptor, FGFR4, which in turn leads to down-regulation of Cyp7a1 in the hepatocyte, leading to decreased bile acid synthesis.

The rate limiting enzyme in bile acids synthesis, cholesterol 7α-hydroxylase (Cyp7a1), is regulated differently in rodents and humans (Ellis E et al, *Hepatology* 27, 615-620 (1998), incorporated by reference herein). The murine promoter of this gene has a response element for LXR which is not present in humans (Chiang J Y et al, *Gene* 262, 257-265 (2001) incorporated by reference herein). As a result, stimulation of LXR by cholesterol leads to a feed-forward regulation that increases the synthesis of bile acids in mice that does not occur in humans. Further, endocrine signaling between the intestine and the liver differ in humans and mice. Humans secrete fibroblast growth factor 19 (FGF19) in response to increases in the ileal bile acid pool which results in a down-regulation of hepatic CYP7A1, the rate-limiting enzyme in bile acid synthesis. In contrast the mouse intestine signals through a different factor, FGF15 (Inagaki T et al, *Cell Metab* 2, 217-225 (2005) and Lundasen T et al, *Intern Med* 260, 530-536 (2006), both of which are incorporated by reference herein.) It is disclosed in the Examples below that human hepatocytes in engrafted mice express CYP7A1 at a 57-fold higher level than in normal human hepatocytes.

The human ortholog of FGF15 is FGF19, similarly produced in the human small intestinal enterocyte, under similar control (excess bile acids activating the nuclear receptor FXR) (Katoh M, *J Mol Med* 12, 45-50 (2003), incorporated by reference herein.) Human hepatocytes have similar bile acid machinery to mouse hepatocytes, with the exception of a co-receptor for FGFR4 called β-Klotho. Because of this different co-receptor, FGF15 generated in the mouse enterocyte does not signal through FGFR4 in the human hepatocyte.

It is disclosed herein that treatment of engrafted mice with human FGF19 restores CYP7A1 expression to that of normal human hepatocytes, suppresses bile acid production resulting in a bile acid profile that is similar that of humans. In that example, mice engrafted with human hepatocytes were treated with recombinant human FGF19. Mice treated with FGF19 showed a marked normalization of the bile acid profile, downregulation of CYP7A1 expression (relative to mice not treated with FGF19), and restoration of EHC signaling. In another example, transgenic mice that express human FGF19 under control of a human FGF19 transcription regulatory apparatus that are engrafted with human hepatocytes also have a bile acid profile similar to that of humans.

I. Abbreviations

ABCG5: ATP-binding cassette G5
ABCG8: ATP-binding cassette G8
AMCA: α-muricholic acid
BMCA: β-muricholic acid
CA: Cholic acid
CDCA: Chenodeoxycholic acid
CYP27A1: Sterol 27-hydroxylase
CYP7A1: Cholesterol 7α-hydroxylase
CYP8B1: Sterol 12α-hydroxylase
DCA: Deoxycholic acid
FRG: triple knock-out mice with deletions of the Fah, Rag2 and common gamma chain of the interleukin receptor [Fah(−/−)Rag2(−/−)Il2rg(−/−)] on the C57Bl/6 background
FRGN: Fah$^{-/-}$/Rag2$^{-/-}$/Il2$^{-/-}$/NOD mouse
FXR: Farnesoid X receptor
GCDCA: glycochenodeoxycholic acid
GDCA: glycodeoxycholic acid
GLCA: glycolithocholic acid
GUDCA: glycoursodeoxycholic acid
HCA: hyocholic acid
HDCA: hyodeoxycholic acid
LCA: Lithocholic acid
NTBC: Nitisinone, 2-2-nitro-4-(trifluoromethyl)benzoyl-cyclohexane-1,3-dione,
OMCA: ω-muricholic acid
SHP: Small heterodimer partner
TCA: taurocholic acid
TCDCA: tarurochenodeoxycholic acid
TDCA: taurodeoxycholic acid
TLCA: taurolithocholic acid
TUDCA: tauroursodeoxycholic acid
UDCA: ursodeoxycholic acid II. Terms and Methods In order to facilitate review of the various embodiments of the invention, the following explanations of specific terms are provided:

Administration: To provide or give a subject an agent, such as a therapeutic agent, by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

Antagonist: A compound (such as drug, protein or small molecule) that counteracts the effects of another compound. In some cases, an antagonist binds to a specific cellular receptor, but does not elicit a biological response.

Bacterial Artificial Chromosome (BAC): A nucleic acid vector derived from the *E. coli* functional fertility plasmid (F-plasmid). Such constructs permit the cloning and transfer of nucleic acid sequences 100 kb or greater and are maintained at a copy number of approximately one copy per cell. BAC vectors comprise one or more bacterial genes that encode proteins for autonomous replication, copy number control, and plasmid partitioning such as oriS, repE, parA, parB, and parC.

Deficient: As used herein, "Fah-deficient" or "deficient in Fah" refers to an animal, such as a mouse, comprising a mutation in Fah, which results in a substantial decrease in, or the absence of, Fah mRNA expression and/or functional FAH protein. As used herein, the term "loss of expression" of functional FAH protein does not refer to only a complete loss of expression, but also includes a substantial reduction in expression of functional FAH protein, such as a reduction of about 80%, about 90%, about 95% or about 99%. In one embodiment, the Fah deficient animal comprises homozygous disruptions, such as homozygous deletions, in the Fah gene. A disruption includes, for example, an insertion, deletion, one or more point mutations, or any combination thereof. As one example, the homozygous deletion is in exon 5 of Fah. In another embodiment, the Fah-deficient animal comprises one or more point mutations in the Fah gene. Examples of suitable Fah point mutations are known in the art (see, for example, Aponte et al, *Proc. Natl. Acad. Sci. U.S.A.* 98, 641-645 (2001), incorporated by reference herein). Similarly, "IL-1R-deficient" or "deficient in IL-1R" refers to an animal, such as a mouse, comprising a mutation in IL-1R, which results in a substantial decrease in, or the absence of, IL-1R mRNA expression and/or functional IL-1R protein. IL-1R knockout mice have been previously described (see, for example, Norman et al, *Ann. Surg* 223, 163-169 (1996) and Glaccum et al, *J Immunol* 159, 3364-3371, 1997) and are commercially available, such as from The Jackson Laboratory (Bar Harbor, Me.). In addition, Rag1-deficient, Rag2-deficient, and IL2rg-deficient refer to animals comprising a mutation in Rag1, Rag2, and IL2rg, respectively, resulting in a substantial reduction in or absence of mRNA expression or production of functional Rag1, Rag2, and/or IL2rg protein. Rag1, Rag2, and IL2rg knockout mice have been previously described and are commercially available.

Engraft: To implant cells or tissues in an animal. As used herein, engraftment of human hepatocytes in a recipient mouse refers to the process of human hepatocytes becoming implanted in the recipient mouse following injection. Engrafted human hepatocytes are capable of expansion in the recipient mouse. As described herein, "significant engraftment" refers to a recipient mouse wherein at least about 1% of the hepatocytes in the liver are human. A "highly engrafted" mouse is one having a liver wherein at least about 60% of the hepatocytes are human. However, engraftment efficiency can be higher, such as at least about 70%, at least about 80%, at least about 90% or at least about 95% or more of the hepatocytes in the mouse liver are human hepatocytes.

FRG mouse: A mutant mouse having homozygous deletions in the fumarylacetoacetate hydrolase (Fah), recombinase activating gene 2 (Rag2) and common-γ chain of the interleukin receptor (IL2rg) genes. Also referred to herein as Fah−/−/Rag2−/−/IL2rg−/−. As used herein, homozygous deletions in the Fah, Rag2 and IL2rg genes indicates no functional FAH, RAG-2 and IL-2Rγ protein is expressed in mice comprising the mutations. One type of FRG mouse is the FRGN mouse which comprises an FRG mouse produced in a NOD (non-obese diabetic) background.

FpmRG mouse: A mutant mouse having homozygous deletions in the recombinase activating gene 2 (Rag2) and common-γ chain of the interleukin receptor (IL2rg) genes, and homozygous point mutations in the fumarylacetoacetate hydrolase (Fah). The point mutation in the Fah gene of FpmRG mice results in mis-splicing and loss of exon 7 in the mRNA (Aponte et al, 2001 supra). Also referred to herein as Fah$^{pm}$/Rag2−/−/IL2rg−/−. As used herein, homozygous deletions in the Rag2 and IL2rg genes indicate no functional RAG-2 and IL-2Rγ protein is expressed in mice comprising the mutations. In addition, mice having homozygous point mutations in the Fah gene do not express functional FAH protein.

Fumarylacetoacetate hydrolase (FAH): A metabolic enzyme that catalyzes the last step of tyrosine catabolism. Mice having a homozygous deletion of the Fah gene exhibit altered liver mRNA expression and severe liver dysfunction (Grompe et al. *Genes Dev* 7, 2298-2307 (1993), incorporated by reference herein). Point mutations in the Fah gene have also been shown to cause hepatic failure and postnatal lethality (Aponte et al, 2001 supra). Humans deficient for Fah develop the liver disease hereditary tyrosinemia type 1 (HT1) and develop liver failure. Fah deficiency leads to accumulation of fumarylacetoacetate, a potent oxidizing agent and this ultimately leads to cell death of hepatocytes deficient for Fah. Thus, Fah-deficient animals can be repopulated with hepatocytes from other species, including humans.

Genetic Alteration: Any mutation in the genome of an animal that results in an altered phenotype. One type of genomic alteration is a disruption. As used herein, a "disruption" in a gene refers to any insertion, deletion or point mutation, or any combination thereof. In some embodiments, the disruption leads to a partial or complete loss of expression of mRNA and/or functional protein. The disruption need not be limited to the coding sequence of the gene itself, but may be in promoter or enhancer sequences of a gene of interest, or may be a disruption in a coding, promoter, or enhancer sequence of a gene encoding a protein that promotes the expression of the gene of interest (such as a transcription factor) or that may be a disruption that promotes the constitutive expression of an inhibitor or suppressor of the gene of interest. A disruption in a gene may be naturally occurring or created artificially (such as with a knockout mutation). Another type of genetic alteration is one that results in the expression of a particular gene. This can take the form of a mutation in a regulatory element or, alternatively, the insertion of a transgene into the genome of an animal where it is expressed by the animal. The transgene need not be native to the host animal. For example, a mouse that expresses human FGF19 is an animal comprising a genetic alteration that results in the expression of human FGF19.

Hepatocyte: A type of cell that makes up 70-80% of the cytoplasmic mass of the liver. Hepatocytes are involved in protein synthesis, protein storage and transformation of carbohydrates, synthesis of cholesterol, bile salts and phospholipids, and detoxification, modification and excretion of exogenous and endogenous substances. The hepatocyte also initiates the formation and secretion of bile. Hepatocytes manufacture serum albumin, fibrinogen and the prothrombin group of clotting factors and are the main site for the synthesis of lipoproteins, ceruloplasmin, transferrin, complement and glycoproteins. In addition, hepatocytes have the ability to metabolize, detoxify, and inactivate exogenous compounds such as drugs and insecticides, and endogenous compounds such as steroids.

Heterozygous: Having dissimilar alleles at corresponding chromosomal loci. For example, an animal heterozygous for a particular gene mutation has the mutation in one allele of the gene but not the other.

Homozygous: Having genetic disruptions at one or more loci. As used herein, "homozygous for disruptions" refers to an organism having disruptions (such as an insertion, deletion or point mutation) in all alleles of a gene. Homozygous disruptions may be identical disruptions on each allele or they may be different disruptions on each gene, all of which disrupt the expression of the gene. In diploid organisms, there are normally two alleles of each gene (one on each chromosome.) However, some organisms may have more than two copies of a particular gene through natural or artificial genomic duplication.

Immunodeficient: Lacking in at least one essential function of the immune system. As used herein, an "immunodeficient" mouse is one lacking specific components of the immune system or lacking function of specific components of the immune system. In one embodiment, an immunodeficient mouse lacks functional B cells, T cells and/or NK cells. In another embodiment, an immunodeficient mouse further lacks macrophages. In some embodiments, an "immunodeficient mouse" comprises one or more of the following genetic alterations: Rag1−/−, Rag2−/−, IL2rg−/−, SCID, NOD and nude. Immunodeficient mouse strains are well known in the art and are commercially available, such as from The Jackson Laboratory (Bar Harbor, Me.) or Taconic (Hudson, N.Y.). In some embodiments, an immunodeficient mouse is a mouse that has been administered one or more immunosuppressants.

Immunosuppression: Refers to the act of reducing the activity or function of the immune system. Immunosuppression can be achieved by administration of an immunosuppressant compound or can be the effect of a disease or disorder (for example, immunosuppression that results from HIV infection or due to a genetic defect).

Macrophage: A cell within the tissues that originates from specific white blood cells called monocytes. Monocytes and macrophages are phagocytes, acting in nonspecific defense (or innate immunity) as well as specific defense (or cell mediated immunity) of vertebrate animals. Their role is to phagocytize (engulf and then digest) cellular debris and pathogens either as stationary or mobile cells, and to stimulate lymphocytes and other immune cells to respond to the pathogen.

Natural Killer (NK) cell: A form of cytotoxic lymphocyte which constitutes a major component of the innate immune system. NK cells play a major role in the host-rejection of both tumors and virally infected cells.

Non-obese diabetic (NOD) mouse: A mouse strain that exhibits susceptibility to spontaneous development of autoimmune insulin dependent diabetes mellitus.

Normalizing bile acid production: In the context of the present disclosure, "normalizing bile acid production" refers to counteracting the phenomenon by which mice engrafted with human hepatocytes (such as FRG mice engrafted with human hepatocytes) display heightened production of total bile acids, a larger liver size, and a more mouse-like bile acid profile. It is disclosed herein that this phenomenon is caused, at least in part, by the overexpression of the human CYP7A1 gene by the engrafted human hepatocytes. Bile acid production in mice engrafted with human hepatocytes need not be identical to the bile acid production and profile typical of human hepatocytes to be "normalized." In some embodiments, normalization of bile acid production is achieved when total bile acid concentration in mice engrafted with human hepatocytes is lower when the mice are treated with FGF19 (relative to engrafted mice that are not treated with FGF19). In particular embodiments, normalization of bile acid production in engrafted mice treated with FGF19 refers to a total bile acid concentration that is about 40%, about 50%, about 60%, about 70%, about 80%, about 90% or about 95% that of an engrafted mouse that is not treated with FGF19. Normalization of bile acid production also refers to a bile acid profile in engrafted mice that is similar to (but need not be identical to) the profile of human hepatocytes. Expression of CYP7A1 in engrafted mice is approximately 80-fold higher than in normal human hepatocytes. The expression level of CYP7A1 in mice engrafted with human hepatocytes need not be identical to the expression level of CYP7A1 in human hepatocytes to achieve normalization of bile acid production. In some embodiments, normalization of bile acid production following treatment with FGF19 results in CYP7A1 expression that is 50-fold higher, 25-fold higher, 10-fold higher, 5-fold higher, 3-fold higher, 1.5-fold higher, or less than 1.1-fold higher than in normal human hepatocytes.

Nude mouse: Refers to a mouse strain with a genetic mutation that causes a deteriorated or absent thymus, resulting in an inhibited immune system due to a greatly reduced number of T cells. The phenotypic appearance of the mouse is a lack of body hair. Nude mice have a spontaneous deletion in the forkhead box N1 (Foxn1) gene.

Recipient: As used herein, a "recipient mouse" is a mouse that has been injected with the isolated human hepatocytes described herein. Typically, a portion (the percentage can vary) of the human hepatocytes engraft in the recipient mouse. In one embodiment, the recipient mouse is an immunodeficient mouse which is further deficient in Fah. In another embodiment, the recipient mouse is a Rag2$^{-/-}$/Il2rg$^{-/-}$ mouse which is further deficient in Fah. In another embodiment, the recipient mouse is an FRG mouse. In another embodiment, the recipient mouse is an FpmRG mouse. In other embodiments, the recipient mouse is an FRG mouse treated with an IL-1R antagonist or an FRG mouse that is further deficient in IL-1R. In still other embodiments, the recipient mouse is an FRGN mouse or an FRG mouse developed on the NOD background.

Recombinase activating gene 1 (Rag1): A gene involved in activation of immunoglobulin V(D)J recombination. The RAG1 protein is involved in recognition of the DNA substrate, but stable binding and cleavage activity also requires RAG2.

Recombinase activating gene 2 (Rag2): A gene involved in recombination of immunoglobulin and T cell receptor loci. Animals deficient in the Rag2 gene are unable to undergo V(D)J recombination, resulting in a complete loss of functional T cells and B cells (Shinkai et al, *Cell* 68, 855-867 (1992); incorporated by reference herein)

Serial transplantation: The process for expanding human hepatocytes in vivo in which hepatocytes expanded in a first mouse are collected and transplanted, such as by injection, into a secondary mouse for further expansion. Serial transplantation can further include tertiary, quaternary or additional mice (Overturf et al, *Am J Pathol* 151, 1273-1280 (1997), incorporated by reference herein).

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage identity or similarity (which takes into account conservative amino acid substitutions); the higher the percentage, the more similar the sequences are. Polypeptides or protein domains thereof that have a significant amount of sequence identity and also function the same or similarly to one another (for example, proteins that serve the same functions in different species or mutant forms of a protein that do not change the function of the protein or the magnitude thereof) can be called "homologs."

Methods of alignment of sequences for comparison are well known in the art. Various programs and alignment algorithms are described in: Smith & Waterman, *Adv Appl Math* 2, 482 (1981); Needleman & Wunsch, *J Mol Biol* 48, 443 (1970); Pearson & Lipman, *Proc Natl Acad Sci USA* 85, 2444 (1988); Higgins & Sharp, *Gene* 73, 237-244 (1988); Higgins & Sharp, *CABIOS* 5, 151-153 (1989); Corpet et al, *Nuc Acids Res* 16, 10881-10890 (1988); Huang et al, *Computer App Biosci* 8, 155-165 (1992); and Pearson et al, *Meth Mol Bio* 24, 307-331 (1994). In addition, Altschul et al, *J Mol Biol* 215, 403-410 (1990), presents a detailed consideration of sequence alignment methods and homology calculations.

The NCBI Basic Local Alignment Search Tool (BLAST) (Altschul et al, (1990) supra) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr database, swissprot database, and patented sequences database. Queries searched with the blastn program are filtered with DUST (Hancock & Armstrong, Comput Appl Biosci 10, 67-70 (1994.) Other programs use SEG. In addition, a manual alignment can be performed. Proteins with even greater similarity will show increasing percentage identities when assessed by this method, such as at least about 75%, 80%, 85%, 90%, 95%, 98%, or 99% sequence identity to a protein.

When aligning short peptides (fewer than around 30 amino acids), the alignment is be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 60%, 70%, 75%, 80%, 85%, 90%, 95%, 98%, or 99% sequence identity to a protein. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least about 60%, 70%, 80%, 90%, 95%, 98%, or 99% sequence identity to a nucleic acid that encodes a protein.

Severe combined immunodeficiency (SCID) mouse: Refers to a strain of mice that is unable to undergo V(D)J recombination and therefore lack functional T cells and B cells. SCID mice also have an impaired ability to activate some components of the complement system. SCID mice are homozygous for the Prkdc$^{scid}$ mutation.

T cell: A type of lymphocyte (a subset of white blood cells) that plays a central role in cell-mediated immunity. T cells are distinguished from other types of lymphocytes, such as B cells and NK cells, by the presence of a special receptor on their cell surface that is called the T cell receptor (TCR). The thymus is generally believed to be the principal organ for T cell development.

Therapeutic agent: A chemical compound, small molecule, or other composition, such as an antisense compound, antibody, protease inhibitor, hormone, chemokine or cytokine, capable of inducing a desired therapeutic or prophylactic effect when properly administered to a subject. As used herein, a "candidate agent" or alternatively a "test compound" is a compound selected for screening to determine if it can function as a therapeutic agent for a particular disease or disorder.

Transgene: An exogenous (heterologous) nucleic acid sequence introduced into a cell or the genome of an organism such as a nucleic acid sequence that codes for FGF19 protein introduced into the genome of a mouse.

Transgenic animal: A non-human animal, usually a mammal, having a transgene present as an extrachromosomal element in a portion of its cells or stably integrated into its germline DNA (i.e., in the genomic sequence of most or all of its cells). The transgene is introduced into the germ line of such transgenic animals by genetic manipulation of, for example, embryos or embryonic stem cells of the host animal according to methods well known in the art. The transgene may be introduced in the form of an expression construct (such as for the production of a "knock-in" transgenic animal or the production of an FGF19 transgenic mouse) or a transgene that upon insertion within or adjacent to a target gene results in a decrease in target gene expression (such as for production of a "knockout" transgenic animal). A "knockout" of a gene is an alteration in the sequence of the gene that results in a decrease of the expression of the target gene, preferably such that target gene expression is undetectable or insignificant. Transgenic knock-out animals can comprise a heterozygous knock-out of a target gene, or a homozygous knock-out of a target gene. "Knock-outs" also include conditional knock-outs, where alteration of the target gene can occur upon, for example, exposure of the animal to a substance that promotes target gene alteration, introduction of an enzyme that promotes recombination at the target gene site (for example, Cre in the Cre-lox system), or other method for directing the target gene alteration postnatally. A homozygous knockout may be abbreviated by indicating the name of the gene and a "−/−". For example, a Fah-knockout may be abbreviated as "Fah$^{-/-}$"

Transplant or transplanting: Refers to the process of grafting an organ, tissue or cells from one subject to another subject, or to another region of the same subject.

Vector: A nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An integrating vector is capable of integrating itself into a host nucleic acid. An expression vector is a vector that contains the necessary regulatory sequences to allow transcription and translation of inserted gene or genes. In one embodiment described herein, the vector comprises a sequence encoding urokinase, such as human urokinase, or comprises a sequence encoding human FGF19. In one embodiment, the vector is a plasmid vector. In another embodiment, the vector is a viral vector, such as an adenovirus vector or an adeno-associated virus (AAV) vector.

Unless otherwise explained, all technical and scientific terms used herein have the same meaning as commonly understood by one of ordinary skill in the art to which this invention belongs. The singular terms "a," "an," and "the"

include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Mouse Models for Engraftment of Human Hepatocytes

Any mouse model with a genetic disruption or that involves the administration of an agent that causes the loss of hepatocyte function may be used to engraft human hepatocytes and therefore may be used in conjunction with FGF19 to normalize bile acid production. The human hepatocytes serve to replace the loss of the mouse hepatocytes resulting from the genetic disruption. In some examples, (U.S. Pat. No. 6,509,514; PCT Publication No. WO 01/07338; U.S. Publication No. 2005-0255591; Dandri et al, Hepatology 33, 981-988 (2001), all of which are incorporated by reference herein) human hepatocytes are engrafted into transgenic animals expressing urokinase plasminogen activator (uPA) under the transcriptional control of an albumin promoter (Sandgren et al, *Cell* 66, 245-256 (1991), incorporated by reference herein). Overexpression of uPA causes metabolic disruption, leading to cell death of the mouse hepatocytes without affecting the transplanted human hepatocytes, which do not express the transgene. The uPA-SCID mouse engrafted with human hepatocytes results in an oversized liver relative to controls (Utoh R et al, *Am J Pathol* 177, 654-665 (2010), incorporated by reference herein).

Another genetic disruption that allows the engrafting of human hepatocytes into a mouse liver is the $Fah^{-/-}$ mouse. FAH is a metabolic enzyme that catalyzes the last step of tyrosine catabolism. Mice having a homozygous deletion of the Fah gene exhibit altered liver mRNA expression and severe liver dysfunction (Grompe et al., *Genes Dev* 7, 2298-2307 (1993), Grompe et al., WO 2008/151283 (2008) and Grompe & Lan, WO 2010/127275 (2010), all of which are incorporated by reference herein.)

Other models that allow engrafting of human hepatocytes include $mdr2^{-/-}$ mice (De Vree J M et al, *Gastroenterology* 119, 1720-1730 (2000) incorporated by reference herein) and mice transgenic for human hepatocyte growth factor (Kay & Ohashi U.S. Pat. No. 6,660,905, (2000); Charlton and Platt, US 2009/0138976 (2005), all of which are incorporated by reference herein). For the former, an mdr2 antagonist may also be administered to the mice to facilitate engraftment.

Additional examples of mouse models that allow engraftment of human hepatocytes into a mouse liver involve the use of a mouse transgenic for Fas-ligand expressed in the liver. In that system, the mice are treated with a Fas-ligand specific antibody and the human hepatocytes are engrafted into the mouse (Takahashi M et al, *Hepatology* 32, 211A (2000) incorporated by reference herein). Other mouse models that allow engraftment of human hepatocytes involve hepatectomy of the host, treatment of the host with hepatotoxic drugs, and host irradiation (C Guha et al, *Artificial Organs* 25, 522-528 (2001) and Weber A et al, *Liver Transplantation* 15, 7-14 (2009) incorporated by reference herein.) Still other models that allow the engraftment of human hepatocytes in a mouse include the Non-alcoholic staetohepatitis (NASH), NOD/Lt-SCID/IL-2R$\gamma^f$, TK-NOG (Hasegawa M, et al, *Biochem Biophys Res Commun* 405, 405-410 (2011), incorporated by reference herein); anti-Fas antibody-treated, SCID/Alb-uPA, FKBP-caspase 8 models, AFC-8 (Washburn M L et al, *Gastroenterology* 140, 1334-1344 (2011); incorporated by reference herein), and others (Nishimura T et al, *Pharmacol Exp Ther* 344, 388-396 (2013), incorporated by reference herein).

In most models, engrafted human hepatocytes are subject to rejection by the host mouse immune system. As a result, models that allow engrafting of human hepatocytes into a mouse host often involve a host mouse that is immunosuppressed in some fashion. Mouse livers have been repopulated with human hepatocytes in a variety of different types of immunodeficient mice, including RAG-2 knockout or SCID mice, both of which lack B cells and T cells (U.S. Pat. No. 6,509,514; PCT Publication No. WO 01/07338; U.S. Patent Publication No. 2005-0255591; all of which are incorporated by reference herein).

In some examples, the model involves the treatment of a $Fah^{-/-}/Rag2^{-/-}/Il2\ rg^{-/-}$ (FRG) mouse with an effective amount of FGF19. Other examples involve an FRG mouse expressing an FGF19 transgene. Such a mouse may be referred to as an FRG/FGF19tg. Still other examples involve a treating $Fah^{-/-}/Rag2^{-/-}/Il2re/NOD$ mouse (FRGN) with an effective amount of FGF19. Other examples involve an FRGN mouse expressing an FGF19 transgene (FRGN/FGF19tg). Other examples involve the treatment of a $Fah^{-/-}/Rag2^{-/-}$ mouse with an effective amount of FGF19. Still other examples involve a $Fah^{-/-}/Rag2^{-/-}$ expressing an FGF19 transgene.

The FRG mouse is known to lack T cells, B cells and NK cells. The engraftment and expansion of human hepatocytes is highly efficient in FRG mice. For example, an FRG mouse can be injected with one million isolated human hepatocytes. Assuming at least 10% efficiency of engraftment, 100,000 or more human hepatocytes can engraft in the recipient mouse. The hepatocytes may also be expanded within an FRG mouse. The number of human hepatocytes that can be isolated following expansion is then about 80 to about 120 million human hepatocytes, which equates to an 800- to 1,200-fold increase.

However, any immunodeficient mouse comprising Fah-deficiency is suitable for use with the methods described herein. In one aspect, the mouse is a $Rag2^{-/-}$ mouse which is deficient in Fah that also expresses or is administered FGF19. In another embodiment, the mouse is a $Rag1^{-/-}$ mouse that is deficient in Fah that also expresses or is administered FGF19. In other embodiments, the mouse is a $NOD/Rag2^{-/-}$ mouse or a $NOD/Rag1^{-/-}$ mouse, either of which is deficient in Fah but also expresses or is administered FGF19. Any of these genotypes may also be $Il1r\gamma^{-/-}$ as well Although some specific combinations of genetic alterations are described herein, other combinations of genetic alterations or treatments resulting in the combination of loss of mouse hepatocyte function, immunodeficiency, and FGF19 expression or administration are contemplated herein. For example, other genetic alterations that cause immunodeficiency include the SCID mutation and the nude mutation and genetic alterations that cause the NOD phenotype.

A Fah-deficient mouse can comprise, for example, homozygous deletions in Fah, or one or more point mutations in Fah. Fah-deficiency (such as by point mutation or homozygous deletion) results in a substantial decrease in, or the absence of, Fah mRNA expression and/or active FAH protein. In addition to the FRG/FGF19tg, a mouse comprising a $Rag2^{-/-}/Il2rg-/-$ genotype homozygous for a point mutation in the Fah gene may also be administered FGF19 or made to express an FGF19 transgene. Without a transgene, this mouse is referred to as the FpmRG mouse. With a transgene that expresses FGF19, this mouse is referred to herein as the FpmRG/FGF19tg mouse.

IV. Normalization of Bile Acid Production

Normalizing bile acid production involves counteracting the phenomenon by which mice engrafted with human hepatocytes (such as FRG mice engrafted with human hepatocytes) display heightened production of total bile acids, an increased intestinal bile acid pool, a larger liver size, and a more mouse-like bile acid profile. It is disclosed herein that this phenomenon is caused, at least in part, by the overexpression of the human CYP7A1 gene by the engrafted human hepatocytes. CYP7A1 is the rate-limiting enzyme in the pathway that results in bile acid synthesis. In the normal human and murine conditions, CYP7A1 expression is downregulated upon a signal from the intestine that sufficient bile acids have been produced. In mice, this signal is the FGF15 protein. Human hepatocytes are non-responsive to FGF15 protein and therefore maintain production of bile acids despite the FGF15 signal being sent from the mouse intestine. In humans, the signal to downregulate CYP7A1 is FGF19, so providing human FGF19 through administration of human FGF19 protein to engrafted mice, the administration of a gene therapy vector expressing FGF19 to engrafted mice, or the creation of engrafted mice that express an FGF19 specific transgene serves to normalize the bile acid profile of mice engrafted with human hepatocytes.

Fibroblast growth factor 19 ((SEQ ID NO: 1, referred to herein as FGF19) is a polypeptide that is the human (and other primate) form of murine FGF15. Current information suggests that FGF19 (and FGF15) bind the coreceptor pair FGF4 and β-klotho. As described above, FGF19 regulates bile acid synthesis as well as gallbladder filling (Fukumoto S, Endocrine J 55, 23-31 (2008), incorporated by reference herein.) FGF19 from monkey, chicken, and other species may also be used.

An effective amount or concentration of an agent in a composition may be any amount or concentration that alone, or together with one or more additional agents is sufficient to achieve a desired effect in a subject. The effective amount of the agent will be dependent on several factors, including, but not limited to, the type of mouse (UPa, FRG, AFC8, TK-NOG, etc.) to which the composition is administered and the manner of administration of the composition. In one example, an effective amount or concentration is one that is sufficient to normalize bile acid production in a mouse engrafted with human hepatocytes.

Bile acid production does not have to be made exactly the same as that of in vitro human hepatocytes or that of human hepatocytes present in a normal human condition for the amount of the composition to be effective. For example, one outcome of normalization of bile acid production is that total bile acid concentration in mice engrafted with human hepatocytes is higher than in mice engrafted with human hepatocytes that have been treated with FGF19. For example, treatment of engrafted mice with 3.0 mg/kg of FGF19 over three days results in a total bile acid concentration that is about 37% that of engrafted mice that were treated with vehicle alone. In some embodiments, the effective amount of FGF19 is an amount that results in a total bile acid concentration that is about 40%, about 50%, about 60%, about 70%, about 80%, about 90% or about 95% that of an engrafted mouse that is not treated with FGF19. Further, in some embodiments, an amount of FGF19 that results in a total bile acid concentration that results in an equivalent total bile acid concentration 5% greater than, 10%, greater than, 20% greater than or 30% greater than normal human bile is an effective amount.

Similarly, expression of CYP7A1 in engrafted mice is approximately 80-fold higher than in normal human hepatocytes. Treatment with FGF19 need not result in CYP7A1 expression exactly the same as that of human hepatocytes for the amount to be effective. In some embodiments, the effective amount of FGF19 results in CYP7A1 expression that is 50-fold higher, 25-fold higher, 10-fold higher, 5-fold higher, 3-fold higher, 1.5-fold higher, or less than 1.1-fold higher than in normal human hepatocytes.

An effective amount of a composition can be administered in a single dose or in several doses (such as daily) over a course of treatment. However, the effective amount can vary depending on the type of subject to which the composition is administered and the mode and manner of administration. For example, a therapeutically effective amount of an agent can vary from about 1 µg-10 mg per kg body weight if administered intravenously.

A non-limiting range for an effective amount of FGF19 within the methods and formulations of the disclosure is about 0.0001 µg/kg body weight to about 10 mg/kg body weight, such as about 0.0001 µg/kg body weight to about 0.001 µg/kg body weight, about 0.001 µg/kg body weight to about 0.01 µg/kg body weight, about 0.01 µg/kg body weight to about 0.1 µg/kg body weight, about 0.1 µg/kg body weight to about 10 µg/kg body weight, about 1 µg/kg body weight to about 100 µg/kg body weight, about 100 µg/kg body weight to about 500 µg/kg body weight, about 500 µg/kg body weight per dose to about 1000 µg/kg body weight, or about 1.0 mg/kg body weight to about 10 mg/kg body weight (or more). One example of an effective amount of FGF19 is a dosage of 0.5 mg/kg given twice daily over a period of three days for a total of 3.0 mg/kg.

The amount given can be varied to maintain a desired concentration. Higher or lower concentrations can be selected based on the mode of delivery, for example, transepidermal, rectal, oral, pulmonary, intranasal delivery, intravenous or subcutaneous delivery. Determination of an effective amount of FGF19 to be administered to a particular type of engrafted mouse of a particular strain may be determined by standard methods and is readily available to one of skill in the art in light of this disclosure.

For administration of FGF19 to a subject such as a mouse engrafted with human hepatocytes, FGF19 is generally combined with an acceptable carrier. In general, the nature of the carrier will depend on the particular mode of administration being employed. The carriers and excipients useful in this disclosure are conventional. See, e.g., Remington: *The Science and Practice of Pharmacy*, The University of the Sciences in Philadelphia, Editor, Lippincott, Williams, & Wilkins, Philadelphia, Pa., 21st Edition (2005). For instance, parenteral formulations usually comprise injectable fluids that include pharmaceutically and physiologically acceptable fluids such as water, physiological saline, balanced salt solutions, aqueous dextrose, glycerol, or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of nontoxic auxiliary substances, such as wetting or emulsifying agents, preservatives, pH buffering agents, and the like, for example sodium acetate or sorbitan monolaurate.

As is known in the art, proteins are often inefficiently administered through ingestion. However, pill-based forms of pharmaceutical proteins may alternatively be administered subcutaneously, particularly if formulated in a slow-release composition. Slow-release formulations may be produced by combining the target protein with a biocompatible matrix, such as cholesterol. Another method of administering proteins is through the use of mini osmotic pumps. As stated above, a biocompatible carrier would also be used in conjunction with this method of delivery. Additional possible methods of delivery include deep lung delivery by inhalation (Edwards et al, *Science* 276, 1868-1871 (1997) and transdermal delivery (Mitragotri et al, *Pharm Res* 13, 411-420 (1996)). FGF19 may be administered in formulation that maintains its effect of normalizing bile acid production in a mouse engrafted with human hepatocytes. Such formulations are readily available to those of skill in the art in light of this disclosure.

FGF19 may be administered by any of a number of modes of administration including topically, orally, intravenously, intramuscularly, intraperitoneally, intranasally, intradermally, intrathecally, subcutaneously, intraocularly, via inhalation, or via suppository. In one example, the compounds are administered to the subject subcutaneously. In another example, the compounds are administered to the subject intravenously.

In some embodiments, the FGF19 is administered as a nucleic acid molecule encoding FGF19 protein. For example, a mouse can be administered a vector encoding FGF19. The vector encoding FGF19 can be any type of vector suitable for delivery to a mouse and capable of expressing the FGF19. Such vectors include viral vectors or plasmid vectors. In one embodiment, the vector is an adenovirus vector. In another embodiment, the vector is an AAV vector. The vector encoding FGF19 can be administered by any suitable means known in the art. In one embodiment, the vector is administered intravenously. In one aspect, the vector is administered by retroorbital injection. In further aspects, the vector is administered intramuscularly or intraperitoneally.

V. Transgenic Mice Expressing Human FGF19

Some embodiments encompass a transgenic mouse that expresses human FGF19 (Fgf19tg) that also allows human hepatocyte engraftment. Such a transgenic mouse would also have a disruption in the expression of a gene that causes the loss of hepatocyte function. Examples of such disruptions include a disruption that causes overexpression of uPA, a disruption that causes a deficiency in the expression of Fah, a disruption that causes the expression of human HGF, or a disruption that causes a deficiency in the expression of mdr2. Such a transgenic mouse can also have a disruption in a gene that renders the mouse immunodeficient. Such a disruption might be one that renders the mouse B cell, T cell and/or NK cell deficient. Examples of disruptions that render a mouse immunodeficient include a mutation in the Rag1 gene, a mutation in the Rag2 gene, a mutation in the Il2rg gene, a scid mutation, a disruption that results in a non-obese diabetic phenotype, a nude mouse mutation, or any combination of these. Examples of potential genotypes of such transgenic mice include $Fah^{-/-}/Rag2^{-/-}/Il2\ rg^{-/-}/Fgf19tg$, $Fah^{-/-}/Rag1^{-/-}/Il2\ rg^{-/-}/Fgf19tg$, $NOD/Fah^{-/-}Rag2^{-/-}/Il2\ rgFgf19tg$, $NOD/Fah^{-/-}/Rag^{-/-}/Il2reFgf19tg$, $Fah^{-/-}/Rag2^{-/-}Fgf19tg$, $Fah^{-/-}/Rag1^{-/-}Fgf19tg$, $NOD/Fah^{-/-}Rag2^{-/-}Fgf19tg$, and $NOD/Fah^{-/-}/Rag1^{-/-}/Fgf19tg$.

The mouse comprises a nucleic acid construct that comprises a nucleic acid sequence that encodes a protein that has the effect of normalizing bile acid production in a mouse engrafted with human hepatocytes with at least 60% sequence identity to FGF19 (SEQ ID NO: 1). The protein may also have at least 70%, at least 80%, at least 90%, at least 95%, at least 96%, at least 97%, at least 98% or at least 99% sequence identity to SEQ ID NO: 1.

The nucleic acid construct may further comprise a promoter that is operably linked to the protein coding sequence in that it is located in an orientation and a distance from the protein such that it drives expression of the protein encoded by the protein coding sequence. The promoter may be any of a number of nucleic acid control sequences that directs transcription of a nucleic acid. Typically, a eukaryotic promoter includes necessary nucleic acid sequences near the start site of transcription, such as, in the case of a polymerase II type promoter, a TATA element or any other specific DNA sequence that is recognized by one or more transcription factors. Expression by a promoter may be further modulated by enhancer or repressor elements. Numerous examples of promoters are available and well known to those of skill in the art. Examples include tissue specific promoters that predominantly transcribe genes in the context of a cell of a particular type or lineage (such as a lymphoid cell, a neuronal cell, a muscle cell, etc.) Other examples include inducible promoters that predominantly transcribe genes in the presence or absence of a particular drug, nutrient, or other compound. In some examples, the promoter is an intestine specific promoter such as the mouse FGF15 promoter. In other examples the promoter is a human FGF19 promoter. In still other examples, the promoter and additional regulatory sequences from the FGF19 locus are included in the nucleic acid construct. Such regulatory sequences may be located anywhere in the genome, including less than 75 kilobases 5' of the FGF19 gene on chromosome 11 or less than 75 kilobases 3' of the FGF19 gene on human chromosome 11, or in one or more of the intronic sequences (SEQ ID NO: 3 and SEQ ID NO: 4) of the FGF19 gene.

In some examples, the protein coding sequence is provided in a bacterial artificial chromosome (BAC) construct. A BAC is a DNA construct derived from a bacterial F-plasmid. Commonly, a BAC includes sequences that allow replication and copy number regulation such as an oriS or a repE-F sequence. It may also include sequences that allow partitioning of the BAC to daughter cells during mitosis such as parA and parB. A BAC may also include a selectable marker such as an antibiotic resistance marker or lacZ. In general, use of a BAC system allows inclusion of several genes, including their entire promoter/enhancer regulatory system because a BAC allows the integration of longer DNA sequences than other plasmid expression systems (often 300 kb or more).

BAC transgenic mice can be generated by pronuclear injection of fertilized mouse oocytes with a purified BAC fragment. The oocytes are then transferred into pseudopregnant foster mothers. Progeny resulting from the oocytes are tested for the presence of the BAC transgene by any of a number of methods known in the art (for example, by PCR detection of the selectable marker.) Positive progeny are backcrossed and the offspring are screened for incorporation of the transgene into the germline. See Marshall V M et al,

*Method Mol Biol* 256, 159-182 (2004), incorporated by reference herein. An FGF-19 transgenic mouse can be bred with mice with genotypes that allow engraftment of human hepatocytes. Through selective breeding and monitoring of the presence of the proper genotypes, an FGF-19 transgenic mouse that may be engrafted with human hepatocytes, such as an FGF19 transgenic FRG mouse or FGF19 transgenic NOD-FRG mouse may be produced.

EXAMPLES

The following examples are illustrative of disclosed methods. In light of this disclosure, those of skill in the art will recognize that variations of these examples and other examples of the disclosed method would be possible without undue experimentation.

Example 1

Methods

Transplantation of FRG mice

FRG mice were maintained as a breeding colony as described previously (Azuma H et al, *Nat Biotechnol* 25, 903-910 (2007), incorporated by reference herein). Mice are maintained on NTBC (Nitisinone, Swedish Orphan International, Stockholm) in the drinking water (16 mg/l). When transplants are performed recipients are injected one time, intraperitoneally with $10^9$ pfu of an adenoviral vector expressing the secreted form of uPA. Recipient animals receive up to 1 million human hepatocytes in 100 microliters of DMEM media via splenic injection with a 27-gauge needle.

Following transplant, NTBC is gradually withdrawn to initiate loss of native hepatocytes at the following schedule: 1.6 mg/l days 0-2; 0.8 mg/l days 3-4, 0.4 mg/l days 5-6 and then completely withdrawn on day 7. For animals that lose in excess of 20% of their body weight, NTBC may be reinstituted for 4-6 days and then gradually withdrawn again. The progress of humanization is monitored monthly in whole blood analysis by ELISA assay for circulating human serum albumin (hSA). In general 1 mg/ml of circulating hSA correlates with ~20% engraftment of human cells, 2 mg with ~40%, and animals with 4 mg are nearly completely (>90%) repopulated. Human hepatocytes were isolated from donor livers not used for transplantation or from pieces of tissue remaining following liver resection for cancer treatment. Hepatocytes were obtained from the Liver Tissue and Cell Distribution System (LTCDS) at the University of Pittsburgh or from commercially available sources and were obtained within 24 hours of isolation. Human hepatocytes (fresh and from serial transplantation) were cold stored in University of Wisconsin (Belzer's) solution for up to 48 hours, allowing additional time for transplants. Serial transplants were conducted as described by Azuma et al supra. At sacrifice, liver tissue was collected and snap frozen in liquid nitrogen for RNA expression analysis, serum was collected for measurement of lipoproteins and bile acid intermediates and gallbladder bile was collected for bile acid analysis.

Lipid analysis

Cholesterol content of serum lipoproteins was separated by size exclusion chromatography from mouse or human serum and was measured via the same method of according to Parini et al, *Eur J Clin Invest* 36, 98-104 (2006), which is incorporated by reference herein.

GC-MS Analysis of Bile Acids in Bile

Bile acids were analyzed as previously described by Bjorkhem I et al, *Scand J Clin Lab Invest* 43, 163-170 (1983), incorporated by reference herein and Ellis et al supra. Briefly, 10 µl of gallbladder bile was diluted with 1 ml of water, 2 ml of 50% EtOH, 1 g KOH and hydrolyzed with 2500 ng deuterium labeled Cholic acid ($D_5$) and chenodeoxycholic acid ($D_4$), Deoxycholic acid ($D_4$), Ursodeoxycholic acid ($D_4$) at 125° C. overnight. The samples were diluted with saline solution and extracted twice with ether to remove neutral steroids. Following acidification with HCl (6M) to pH 1, bile acids were extracted with ether. The ether phase methylated with trimethylsilyldiazomethane (Sigma cat.: 36,283-2) and silylated using hexamethyl-disilazane (Alfa Aesar L16519) and trimethylchlorosilane (Merck 1.02333.0100) in pyridine at 60° C. for 30 minutes. The solvent was evaporated and the samples dissolved in 200 µl of hexane and analyzed by GC-MS (Agilent 5973 6890N). Data was analyzed using Agilent Mass Hunter® software.

LC-MS/MS Analysis of Bile Acid Conjugates in Bile

Bile acids were analyzed using HPLC-MSMS using a modified method initially described by Tagliacozzi D et al, *Clin Chem Lab Met* 41, 1633-1641 (2003), which is incorporated by reference herein. A 2 µl volume of bile was mixed with 800 ng internal standards in 40 µl methanol and 800 µl acetonitrile and vortexed for 1 minute. The mixture was centrifuged at 13 000×g for 15 minutes and the upper phase was transferred to a disposable glass centrifuge tube and evaporated under $N_2$. The residue was dissolved in 75 µl of methanol, vortexed and transferred to Waters® vials. The glass centrifuge tube was rinsed again with 75 µl of 40% Methanol in water, 0.02% Formic acid and 10 mM Ammonium acetate and pooled into a Waters® vial. A Waters LC-MS/MS Micromass Quattro Micro®, equipped with a C18 reverse-phase column and ESI in negative mode was used for analysis. Six different deuterium labeled internal standards ($D_5$-CA, $D_4$-UDCA, $D_4$-LCA, $D_4$-GCA, $D_4$-GUDCA, $D_4$-GLCA), and unlabeled unconjugated bile acids (LCA, DCA, CDCA, HDCA, UDCA, CA, HCA, BMCA, AMCA and OMCA) and glycine—as well as taurine—conjugated bile acids (GLCA, GDCA, GCDCA, GCA, GUDCA, TLCA, TDCA, TCDCA, TCA, TUDCA) were used for calibration and quantification. Unconjugated bile acids were measured by molecular anions (no product ions are produced). Glycine- or taurine-conjugated bile acids were quantified from negative daughter ions, generated after loss of the conjugate.

FGF19 Administration

Twelve FRG mice were used in this experiment, six of which received intrasplenic human hepatocyte transplants with resultant repopulation of these livers, and six that were used as controls. When the transplanted mice were repopulated with human hepatocytes as assessed by serum human albumin levels, the FGF19 administration experiment was performed. Recombinant human FGF-19 (PeproTech, Catalog #100-32) was reconstituted in 0.9% saline with 0.1% BSA as recommended by the manufacturer. Three humanized and three control FRG mice were injected subcutaneously with 0.5 mg/kg FGF-19 twice daily for three days. Simultaneously three humanized and three control FRG mice were injected with the identical diluent absent FGF19. The mice were killed between 1-3 hours after the final injection, after their gallbladders had been cannulated for a 15-20 minute collection of bile. Serum and liver were harvested and snap frozen in liquid nitrogen.

RNA

RNA was extracted using Tri Reagent (Invitrogen cat#: 15596-026) according to the manufacturer's instructions. Integrity was checked on a 1% agarose gel with 1×TAE and concentration measured using the Nano Drop ND-1000® spectrophotometer.

CDNA Synthesis

A high capacity cDNA reverse transcription kit from Applied Biosystems (cat#4374966) with RNAse inhibitor was used according to the manufacturer's instructions.

QPCR

RNA expression was quantified using a real time PCR machine (ABI Prism 7000®). For human genes, predesigned Taqman probes were used. hCyp8B1: Hs00244754_s1, hCyp27A1: Hs00168003_m1, hCyp7A1: Hs00167982_m1, hCyc (PPIA): Hs99999904_m1, hSHP: Hs00222677_m1, hFGF19: Hs 00192780_m1, hABCB11: HS00184824_m1, hNTCP: HS00161820_m1, hFXR: Hs00231968_m1.

For mouse genes real time PCR was performed and quantified through SYBR Green incorporation. The following primer sequences were used:

```
mCyclophilin Fw:
                                   SEQ ID NO: 14
GAT GAG AAC TTC ATC CTA AAG CAT ACA - mCyclophilin Rev:
                                   SEQ ID NO: 15
TCA GTC TTG GCA GTG CAG ATA AA -, mCYP7A1 Fw:
                                   SEQ ID NO: 16
AGC AAC TAA ACA ACC TGC CAG TAC TA -, mCYP7A1 Rev:
                                   SEQ ID NO: 17
GTC CGG ATA TTC AAG GAT GCA -, mGAPDH Fw:
                                   SEQ ID NO: 18
TGT GTC CGT CGT GGA TCT GA - mGAPDH Rev:
                                   SEQ ID NO: 19
CCT GCT TCA CCA CCT TCT TGA T - mABCG5 Fw:
                                   SEQ ID NO: 20
TGG ATC CAA CAC CTC TAT GCT AAA - mABCG5 Rev:
                                   SEQ ID NO: 21
GGC AGG TTT TCT CGA TGA ACT G - mABCG8 Fw:
                                   SEQ ID NO: 22
TGC CCA CCT TCC ACA TGT C - mABCG8 Rev:
                                   SEQ ID NO: 23
ATG AAG CCG GCA GTA AGG TAG A - mSHP-Fw:
                                   SEQ ID NO: 24
AAG GGC ACG ATC CTC TTC AA - mSHP-Rev:
                                   SEQ ID NO: 25
CTG TTG CAG GTG TGC GAT GT -
```

Statistics

When appropriate, data were analyzed either by the non-parametric Mann-Whitney U test, the nonparametrici Kruskal-Wallis test or by 1-way ANOVA followed by post-hoc comparison according to Dunett or to LSD tests. In order to stabilize variances, data were transformed prior to ANOVA.

Example 2

Bile Acid Conjugates

Bile acids are conjugated in hepatocytes prior to excretion into bile. The conjugation of bile acids differs significantly between species; mice conjugate almost exclusively with taurine whereas humans conjugate with both glycine and taurine at a ratio of approximately 5:1. In mice repopulated with human hepatocytes one could therefore expect to find glycine conjugated bile acids. Bile acid conjugates were analyzed in mouse bile using LC-MS/MS. Table 1 shows the percentages of taurine conjugated cholic acid (T-CA), glycine conjugate cholic acid (G-CA) and unconjugated cholic acid (CA) in humanized and control mice. The results showed that in highly repopulated mice (88-94% humanized) the proportion of T-CA was decreased and both free CA and G-CA appeared.

TABLE 1

LC-MS/MS analysis of conjugates of cholic acid in gallbladder bile of control FRG mice and of mice repopulated at different percentages of human liver cells. Data show the percentages of taurine conjugated cholic acid (T-CA), glycine conjugated cholic acid (G-CA), and free cholic acid (CA).

| Mouse ID | % Humanized Cells | % T-CA | % G-CA | % CA |
|---|---|---|---|---|
| FRG 10 | 0 | 99.8 | 0.17 | 0.02 |
| FRG 1 | 0 | 98.6 | 0.15 | 1.30 |
| FRG 2 | 0 | 99.4 | 0.11 | 0.52 |
| TxFRG 2 | 94 | 80.8 | 8.11 | 11.07 |
| TxFRG 4 | 90 | 81.5 | 6.96 | 11.53 |
| TxFRG 5 | 88 | 87.4 | 1.50 | 11.12 |
| TxFRG 8 | 78 | 99.4 | 0.47 | 0.08 |
| TxFRG 11 | 45 | 95.7 | 0.14 | 4.11 |

Example 3

Bile Acid Composition in mice with humanized livers

Bile acid composition in mice differs from that of humans by the presence of additional bile acids in mice: α, β and ω-muricholic acid, with β—as the predominant form. Rodents also have the capacity to re-hydroxylate bile acids that have been de-hydroxylated in the intestine producing the secondary bile acid deoxycholic acid (DCA). Humans do not re-hydroxylate and therefore have higher levels of secondary bile acids such as DCA. Following hydrolysis, bile acids were extracted from 1 μl of bile and analyzed by GC-MS. Table 2 shows the levels of individual bile acids and the ratio of DCA to β-muricholic acid (BMCA) for each sample. Table 3 shows the ratio of DCA/BMCA from non-transplanted mice was significantly different in highly repopulated mice <80%, (p=0.063) as well as in moderately repopulated mice 50-80%, p=0.026. In mice with a low degree of repopulation (30-50%), the ratio of DCA/BMCA was not significantly different from non-transplanted animals. Statistics were performed by a 1-way ANOVA on log-transformed data followed by Dunett's test. The overall significance was p=0.023 (all different vs. control).

TABLE 2

Total bile acid concentration in gallbladder bile collected from control mice with or without injection of FGF19. Statistics were performed on log transformed data in order to stabilize variances prior to one way ANOVA followed by post-hoc analysis according to the least significance difference (LSD) test. The overall significance of the experiment was p = 0.0048.

| Mouse ID | % of Human | DCA | CDCA | AMCA | CA | UDCA | HCA | BMCA | OMCA | DCA/BMCA |
|---|---|---|---|---|---|---|---|---|---|---|
| TxFRG1 | 90 | 73 | 4 | 0 | 14 | 2 | 0 | 7 | 0 | 10.36 |
| TxFRG2 | 94 | 17 | 7 | 12 | 42 | 4 | ND | 18 | ND | 0.98 |
| TxFRG3 | 86 | 1 | 3 | 6 | 47 | 1 | 0 | 35 | 7 | 0.02 |
| TxFRG4 | 90 | 20 | 1 | 1 | 70 | 0 | 1 | 7 | 2 | 2.98 |
| TxFRG5 | 88 | 5 | 4 | 5 | 74 | 1 | 0 | 11 | 0 | 0.47 |
| TxFRG6 | 79 | 8 | 9 | 8 | 67 | 2 | 0 | 7 | 0 | 1.19 |
| TxFRG7 | 78 | 13 | 1 | 0 | 79 | 0 | 0 | 6 | 1 | 2.25 |
| TxFRG8 | 78 | 9 | 2 | 3 | 61 | 1 | ND | 25 | ND | 0.36 |
| TxFRG9 | 70-80 | 3 | 2 | 3 | 61 | 1 | 0 | 19 | 11 | 0.14 |
| TxFRG10 | 70-80 | 4 | 0 | 1 | 92 | 0 | 0 | 2 | 0 | 2.71 |
| TxFRG11 | 45 | 10 | 5 | 3 | 54 | 2 | ND | 26 | ND | 0.38 |
| TxFRG12 | 30 | 1 | 2 | 3 | 68 | 1 | 1 | 19 | 6 | 0.07 |
| TxFRG13 | 30 | 8 | 2 | 9 | 60 | 3 | ND | 17 | ND | 0.47 |
| FRG1 | 0 | 0 | 1 | 2 | 62 | 1 | 0 | 24 | 9 | 0.02 |
| FRG2 | 0 | 0 | 1 | 3 | 59 | 1 | 1 | 15 | 21 | 0.03 |
| FRG3 | 0 | 3 | 4 | 11 | 48 | 5 | ND | 29 | ND | 0.10 |
| FRG4 | 0 | 2 | 5 | 8 | 56 | 2 | ND | 27 | ND | 0.10 |
| FRG5 | 0 | 2 | 6 | 2 | 43 | 2 | ND | 45 | ND | 0.04 |
| FRG6 | 0 | 2 | 16 | 0 | 36 | 1 | ND | 45 | ND | 0.04 |
| FRG7 | 0 | 4 | 31 | 0 | 28 | 1 | ND | 36 | ND | 0.10 |
| FRG8 | 0 | 2 | 6 | 10 | 57 | 4 | ND | 21 | ND | 0.08 |
| FRG9 | 0 | 1 | 8 | 1 | 62 | 2 | ND | 26 | ND | 0.05 |
| FRG10 | 0 | 2 | 7 | 10 | 31 | 6 | ND | 44 | ND | 0.05 |

ND = Not determined.
% of Human = % of humanized cells

Example 4

Figure 1:
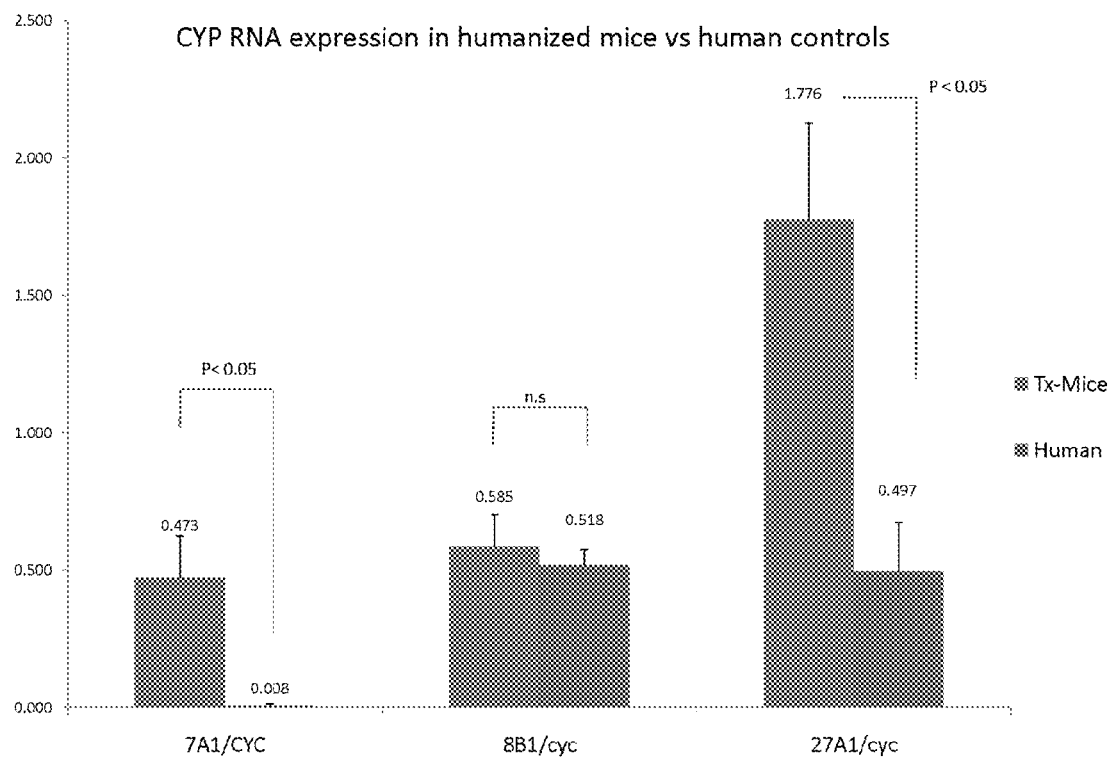
FIG. 1 is a graph of the mRNA expression of CYP7A1, CYP8B1, and CYP27A1 in human hepatocytes collected from engrafted FRG mice (Tx-mice, left bars) and normal humans (right bars). Expression was measured by quantitative real time PCR. Values are normalized to the expression of the human cyclophilin housekeeping gene.
Figure 2:
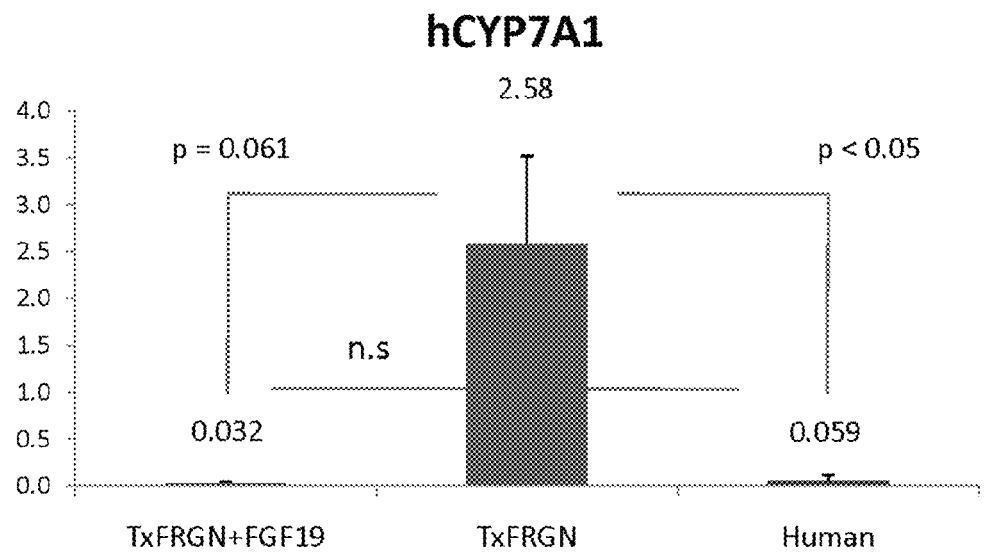
FIG. 2 is a graph of the mRNA expression of human CYP7A1 in engrafted FRGN mice treated with recombinant human FGF19 (hFGF19) (TxFRGN+FGF19) in hepatocytes compared to that of untreated engrafted FRGN mice (Tx-FRGN) and normal human hepatocytes (human).
Figure 3:
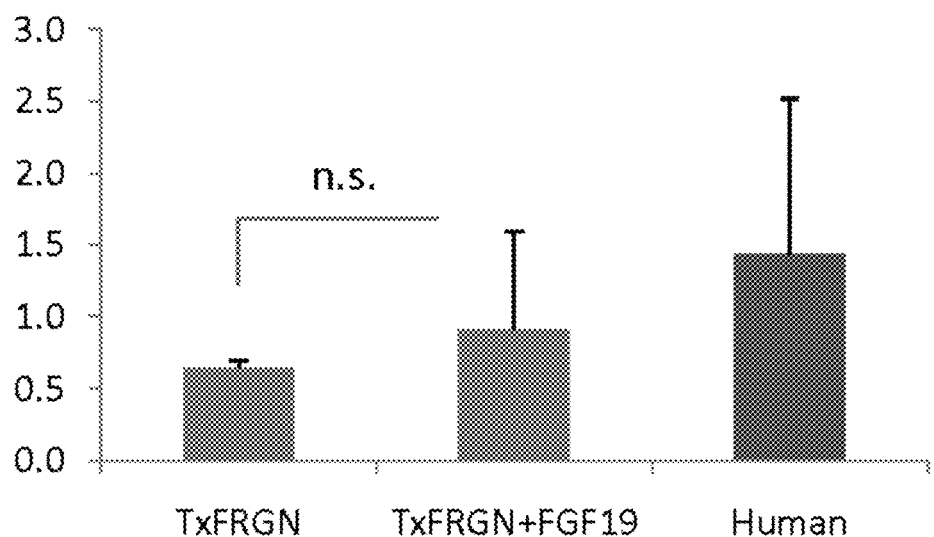
FIG. 3 is a graph of the mRNA expression of human CYP8B1 in engrafted FRGN mice treated with hFGF19 (TxFRGN+FGF19) in hepatocytes compared to that of untreated engrafted FRG mice (TxFRGN) and normal human hepatocytes (human).
Figure 4:
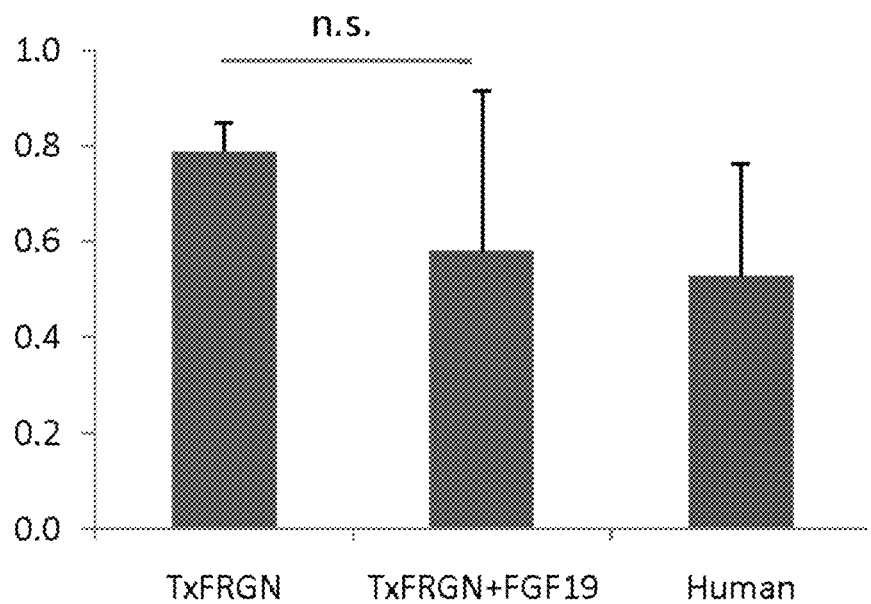
FIG. 4 is a graph of the mRNA expression of human CYP27A1 in engrafted FRGN mice treated with hFGF19 (TxFRGN+FGF19) in hepatocytes compared to that of untreated engrafted FRGN mice (TxFRGN) and normal human hepatocytes (human).

RNA Expression of Human Bile Acid Synthesis Enzymes in Mice with Humanized Livers Relative to Expression in Normal Human Hepatocytes In FIG. 1, expression of the rate limiting enzyme in the bile acid synthesis Cholesterol 7a-hydroxylase, also called CYP7A1, was approximately 57-fold higher in humanized mice relative to humans. CYP7A1 expression in human liver was measured at a value of 0.008 arbitrary units (n=5) relative to 0.473 in humanized mice. This difference was statistically significant with $p<0.05$. The expression of Sterol 27A1-hydroxylase (CYP27A1), the enzyme that catalyzes the side chain degradation and the first step of the acidic pathway of bile acid synthesis, was also significantly higher in humanized mice, but not to the same magnitude with a value of 0.5 (arbitrary units) in humans (n=5) and a value of 1.8 in humanized mice (n=3), $p<0.05$. The expression of Sterol 12β-hydroxylase (CYP8B1), the enzyme responsible for the formation of cholic acid (and subsequently deoxycholic acid), was not significantly different in humanized mice (0.58) compared to human controls (FIG. 3). Statistics were performed by a non-parametric Mann-Whitney U test.

Example 5

Administration of FGF19 Gives Mice Treated with Human Hepatocytes a More Phenotypically Human Bile Acid Profile Recombinant human FGF19, 0.5 mg/kg body weight, was injected subcutaneously twice daily for 3 days into humanized (TxFRG) mice or non-humanized FRG controls. The experiment was terminated 5 hours after the last injection. Bile was collected over a 15 minute period and the liver was snap frozen for use in RNA expression analysis. Administration of FGF19 caused a reduction in the total bile acid concentration in bile of humanized mice, from 24,500 ng/µl to 9,000 ng/µl, p=0.001 relative to non-humanized controls. Non-transplanted mice injected with FGF19 also exhibited the same effect decreasing from 17,300 ng/µl to 9,450 ng/µl after infusion (p=0.01). Data are summarized in Table 3.

TABLE 3

Total bile acid concentration in gallbladder bile collected from control mice or humanized mice. Mice were treated with either FGF19 or vehicle. Statistics were performed on log-transformed data in order to stabilize variances prior to one-way ANOVA. This was followed by post-hoc analysis according to the least significance difference (LSD) test. The overall significance of the experiment was p = 0.0048. Controls are FRG mice without human hepatocytes added.

| Subj# | Condition | Tx | Deoxy % | Cheno % | Alpha muri % | Chol % | Urso % | Hyochol % | Beta muri % | Omega muri % | DCA/BMCA | Total Bile Acid ng/µl |
|---|---|---|---|---|---|---|---|---|---|---|---|---|
| 1 | Humanized | FGF19 | 0.2 | 1.9 | 4.8 | 42.0 | 1.3 | 1.0 | 41.6 | 7.2 | 0.01 | 7431 |
| 2 | Humanized | FGF19 | 0.9 | 2.9 | 7.2 | 21.0 | 2.2 | 0.7 | 55.3 | 9.9 | 0.02 | 10986 |
| 3 | Humanized | FGF19 | 0.0 | 0.4 | 0.2 | 90.7 | 0.1 | 0.9 | 3.6 | 4.0 | 0.00 | 8593 |
| | | | | | | | | | | | Avg (1-3) | 9003 |

TABLE 3-continued

Total bile acid concentration in gallbladder bile collected from control mice or humanized mice. Mice were treated with either FGF19 or vehicle. Statistics were performed on log-transformed data in order to stabilize variances prior to one-way ANOVA. This was followed by post-hoc analysis according to the least significance difference (LSD) test. The overall significance of the experiment was p = 0.0048. Controls are FRG mice without human hepatocytes added.

| Subj# | Condition | Tx | Deoxy % | Cheno % | Alpha muri % | Chol % | Urso % | Hyochol % | Beta muri % | Omega muri % | DCA/BMCA | Total Bile Acid ng/μl |
|---|---|---|---|---|---|---|---|---|---|---|---|---|
| 4 | Humanized | Vehicle | 0.6 | 6.5 | 9.3 | 32.6 | 4.4 | 0.5 | 29.4 | 16.7 | 0.02 | 19065 |
| 5 | Humanized | Vehicle | 7.1 | 3.8 | 2.9 | 78.5 | 1.8 | 0.3 | 4.2 | 1.4 | 1.72 | 27861 |
| 6 | Humanized | Vehicle | 17.4 | 3.0 | 3.1 | 66.6 | 2.5 | 0.3 | 3.8 | 3.3 | 4.58 | 26626 |
|   |           |         |     |     |     |      |     |     |     |     | Avg (4-6) | 24517 |
| 7 | Control | FGF19 | 0.6 | 0.9 | 2.4 | 30.0 | 5.1 | 1.4 | 21.7 | 38.0 | 0.03 | 9149 |
| 8 | Control | FGF19 | 0.8 | 0.9 | 2.5 | 30.7 | 4.9 | 1.4 | 22.8 | 36.0 | 0.04 | 9228 |
| 9 | Control | FGF19 | 0.9 | 0.9 | 2.4 | 30.5 | 5.3 | 1.2 | 22.1 | 36.8 | 0.04 | 9984 |
|   |         |       |     |     |     |      |     |     |     |     | Avg (7-9) | 9454 |
| 10 | Control | Vehicle | 0.5 | 0.8 | 3.8 | 45.7 | 0.8 | 0.5 | 39.2 | 8.7 | 0.01 | 16495 |
| 11 | Control | Vehicle | 0.0 | 0.4 | 1.9 | 73.2 | 0.3 | 0.6 | 19.1 | 4.5 | 0.00 | 13552 |
| 12 | Control | Vehicle | 0.9 | 0.9 | 4.1 | 42.5 | 1.2 | 0.4 | 40.2 | 9.8 | 0.02 | 21819 |
|   |         |         |     |     |     |      |     |     |     |     | Avg (10-12) | 17289 | p < 0.001 for Avg (1-3) compared to Avg (4-6)
p < 0.01 for Avg (7-9) compared to Avg (10-12)

Figure 5:
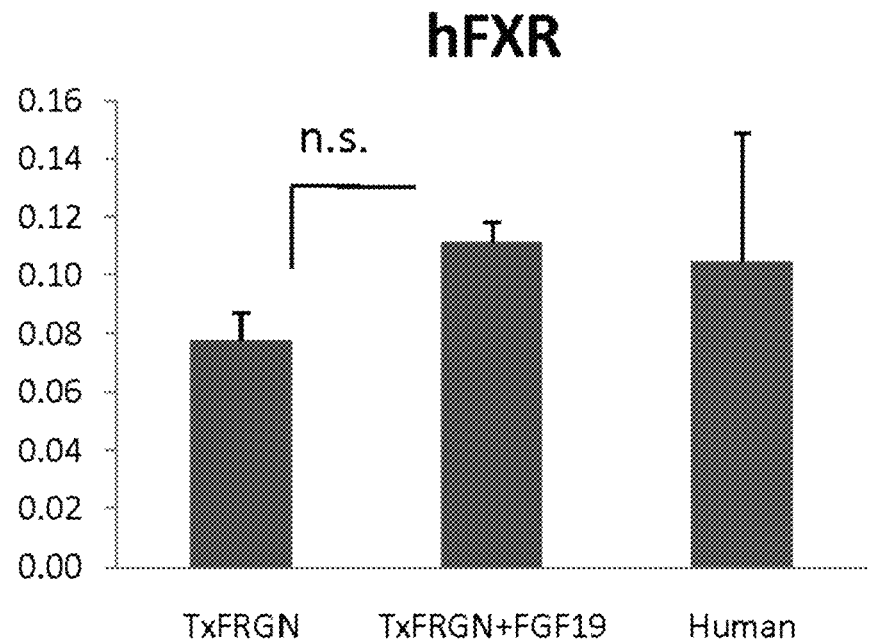
FIG. 5 is a graph of the mRNA expression of human FXR in engrafted FRGN mice treated with hFGF19 (TxFRGN+FGF19) in hepatocytes compared to that of untreated engrafted FRGN mice (TxFRGN) and normal human hepatocytes (human).

As shown in FIG. 5, the expression of human CYP7A1 was markedly lower (about 80-fold) in engrafted mice treated with FGF19 relative to engrafted mice not treated with FGF19. FRG engrafted with human hepatocytes have an mRNA expression level of CYP7A1 of 2.58 (arbitrary units), while non-engrafted FRG mice treated with FGF19 have an expression level of 0.032. The p value of the comparison between the two groups is 0.061. The expression of CYP7A1 in FGF19 treated FRG mice with human hepatocytes was similar to that of normal human hepatocytes procured directly from a human donor. Data were analyzed by a non-parametric Kruskal-Wallis ANOVA. The overall significance of the experiment was p<0.05.

Figure 6:
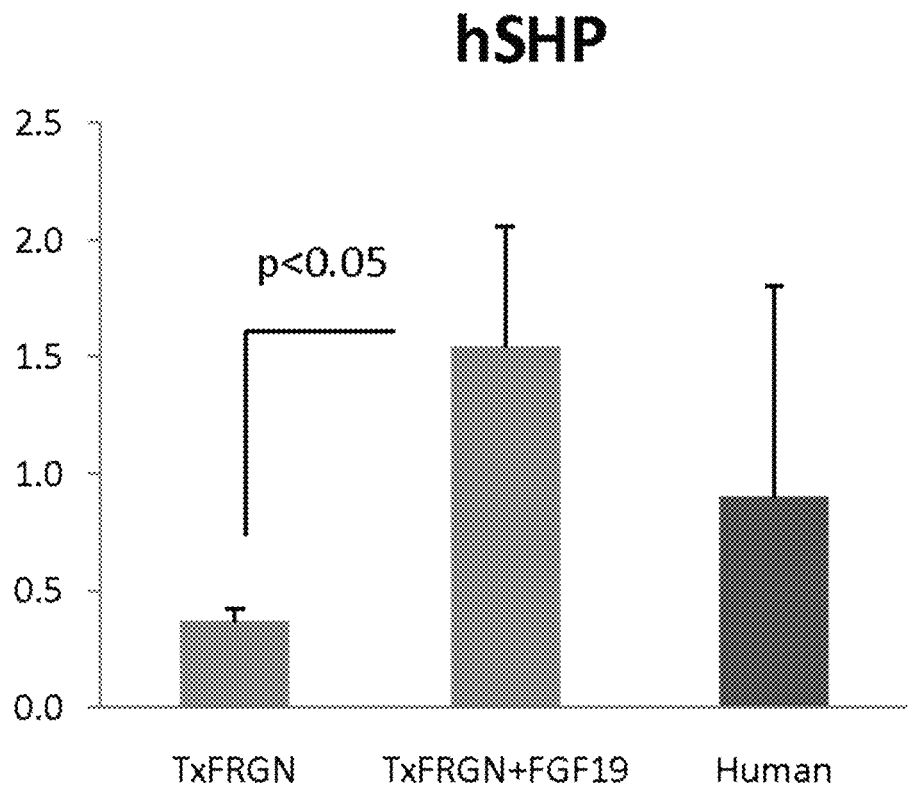
FIG. 6 is a graph of the mRNA expression of human SHP in engrafted FRG mice treated with hFGF19 (TxFRGN+ hFGF19) in hepatocytes compared to that of untreated engrafted FRGN mice (TxFRGN) and normal human hepatocytes (human).
Figure 7:
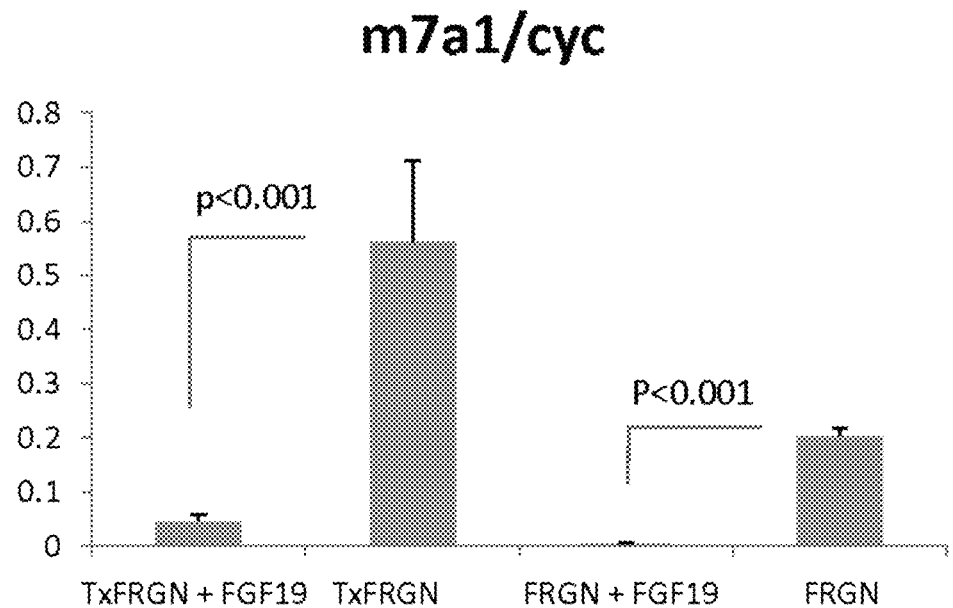
FIG. 7 is a graph of the mRNA expression of mouse Cyp7a1 normalized to cyclophilin (m7a1/cyc) in the livers of engrafted FRGN mice treated with hFGF19 (TxFRGN+ FGF19), engrafted FRGN mice not treated with hFGF19 (TxFRGN), non-engrafted FRGN mice treated with hFGF19 (FRGN+FGF19) and non-engrafted FRGN mice not treated with hFGF19 (FRGN). MRNA expression is measured by quantitative real time PCR.
Figure 8:
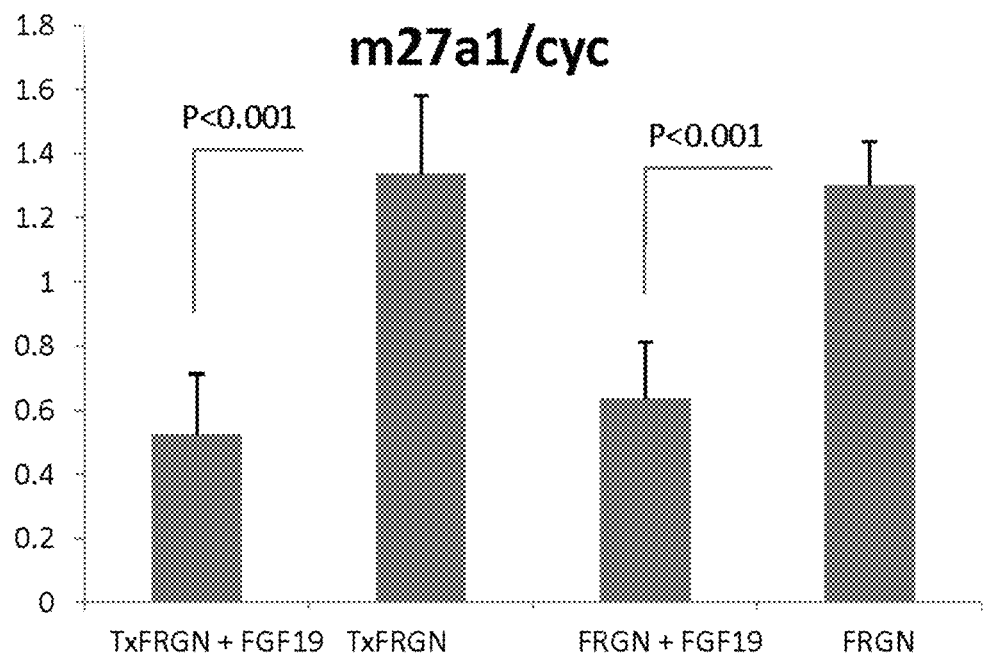
FIG. 8 is a graph of the mRNA expression of mouse Cyp27a1 normalized to cyclophilin (m27a1/cyc) in the livers of engrafted FRGN mice treated with hFGF19 (Tx-FRGN+FGF19), engrafted FRGN mice not treated with hFGF19 (TxFRGN), non-engrafted FRGN mice treated with hFGF19 (FRGN+FGF19) and non-engrafted FRGN mice not treated with hFGF19 (FRGN). Messenger RNA expression is measured by quantitative real time PCR.
Figure 9:
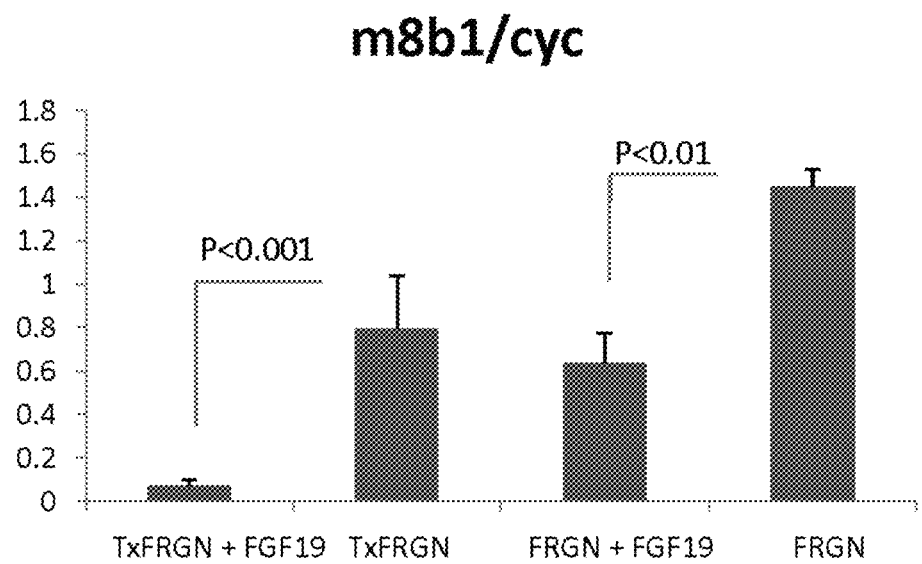
FIG. 9 is a graph of the mRNA expression of mouse Cyp8b1 normalized to cyclophilin (m8b1/cyc) in the livers of engrafted FRGN mice treated with hFGF19 (TxFRGN+ FGF19), engrafted FRGN mice not treated with hFGF19 (TxFRGN), non-engrafted FRGN mice treated with hFGF19 (FRGN+FGF19) and non-engrafted FRGN mice not treated with hFGF19 (FRGN). MRNA expression is measured by quantitative real time PCR.
Figure 10:
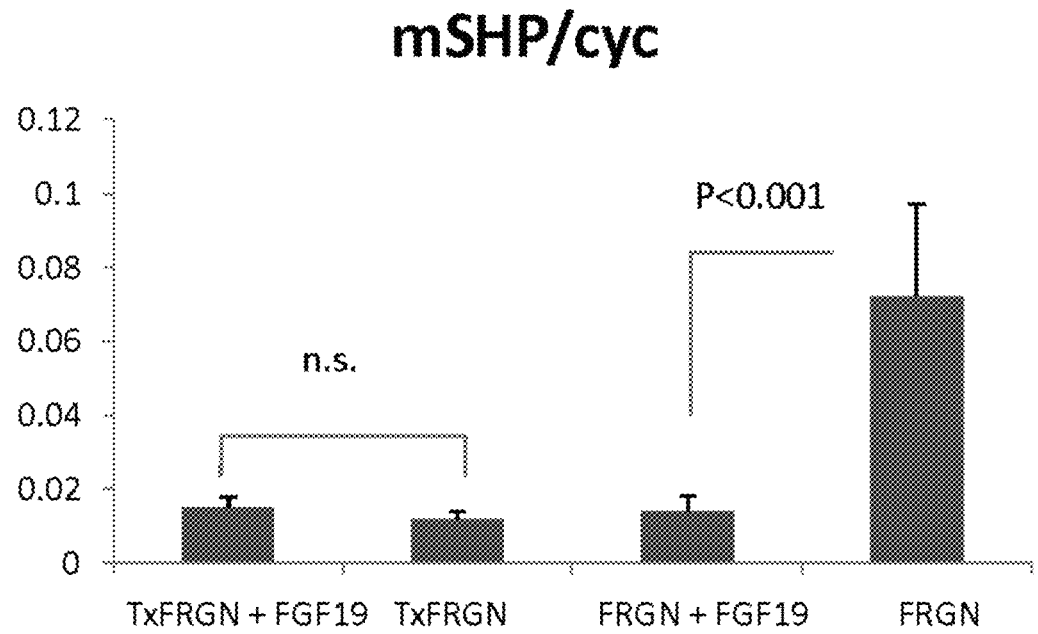
FIG. 10 is a graph of the mRNA expression of mouse SHP normalized to cyclophilin (mSHP/cyc) in the livers of engrafted FRGN mice treated with hFGF19 (TxFRGN+ FGF19), engrafted FRGN mice not treated with hFGF19 (TxFRGN), non-engrafted FRGN mice treated with hFGF19 (FRGN+FGF19) and non-engrafted FRGN mice not treated with hFGF19 (FRGN). mRNA expression is measured by quantitative real time PCR.

The RNA expression of human CYP8B1, human CYP27A1 and the human nuclear receptors short heterodimer partner (SHP) and farnesoid x receptor protein (FXP) are shown in FIG. 3, FIG. 4, FIG. 5, and FIG. 6 respectively. No statistically significant differences were observed with regard to the expression of human CYP8B1, human CYP27A1, and human FXR resulting from the administration of FGF19. Expression of human SHP was significantly lower in FGF19 treated humanized FRG relative to untreated humanized FRG (p<0.05) (FIG. 6). FGF19 treated humanized FRG also expressed significantly less mouse Cyp7a1 (p=0.001) relative to either humanized or non-humanized mice not treated with FGF19 (n=3) (FIG. 7). This indicates that human FGF19 can signal in mouse hepatocytes. Expression of mouse Cyp8b1 and mouse Cyp27a1 were also markedly lower in FGF19 treated animals relative to controls (FIG. 8 and FIG. 9). FGF19 had no effect on mouse SHP expression in humanized mice, but was markedly lower in FGF19 treated, non-humanized mice relative to the control (FIG. 10).

Example 6

Generation of an FGF19 transgenic mouse

Figure 12:
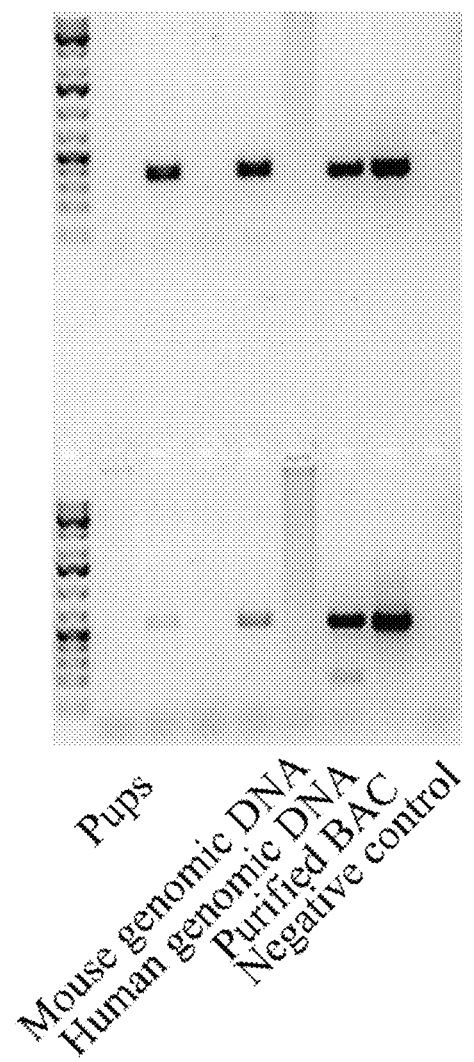
FIG. 12 is an image of a polyacrylamide gel showing the genotypes of four mouse pups each of which is positive for the BAC shown in FIG. 11. The top lanes contain amplifications of region P3 in the map in FIG. 11. The bottom lanes contain amplifications of P1. The final four lanes contain the indicated controls.

Two mouse models with an FGF19 transgene have been produced (Nicholes K et al, *Am J Pathol* 160, 2295-2307 (2002), Tomlinson E et al, *Endocrinology* 143, 1741-1747 (2002) both of which are incorporated by reference herein) but in these cases the transgene was under the control of artificial promoters (myosin light chain and metallothionein promoters, respectively.) An FGF19 transgenic mouse in which FGF19 is under its endogenous transcriptional control and therefore properly regulated to ensure normalization of bile acid synthesis was produced. The transgenic mouse comprising approximately 150 kb of human chromosome 11 integrated into its genome, including the genomic sequence of FGF19 as well as the surrounding genomic DNA, including promoter and all other transcriptional control regions less than 75 kb 5' and less than 75 kb 3' of FGF19. The human DNA sequence was introduced into the mouse genome through the insertion of a bacterial artificial chromosome (BAC, RP11-124K14). FIG. 11 shows a schematic of the BAC and indicates the primers used to detect its presence in transgenic mice. FIG. 12 shows a genotyping gel with amplification of 2 regions in the integrated BAC in a litter of transgenic pups. The amplified regions are sufficiently distant from one another to ensure that the entire BAC was integrated into the genomes of the transgenic mice.

Example 7

Tissue Specific FGF19 Expression and Regulation in Transgenic Mice is Confirmed

Figure 13:
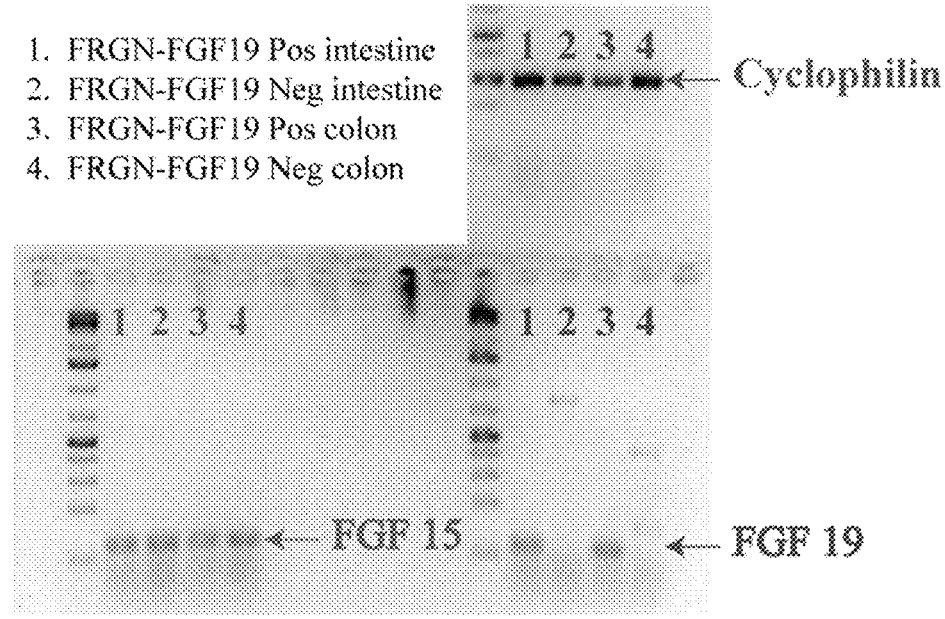
FIG. 13 is an image of a polyacrylamide gel indicating amplified FGF15, cyclophilin, and FGF19 from intestine and colon of FRGN mice and FRGN-FGF19 transgenic mice as indicated.

Tissue-specific FGF19 expression is demonstrated in the FGF19 transgenic mouse. Table 4 shows the results of quantitative PCR (qPCR) for mouse FGF15 and human FGF19 mRNA. Expression levels are the Ct of the PCR reaction relative to the Ct of the housekeeping gene cyclophilin. FIG. 13 shows an agarose gel upon which the qPCR products were run. Note that bands corresponding to the size of human FGF19 are present in the FGF19 transgenic mouse tissues, while there are no bands in the non-transgenic littermate tissues.

TABLE 4

Results of quantitative PCR from FGF19 transgenic mice. Values are normalized to Cyclophilin expression via the following formula: $\{[1/(Ct_{FGF}/Ct_{Cp})] - [1/(40/Ct_{Cp})]\} * 100$ Where $Ct_{FGF}$ is the Ct of FGF15 or FGF19 as indicated, $Ct_{Cp}$ is the Ct of Cyclophilin. 40 is the maximal number of cycles run.

| Tissue | FGF15 | FGF19 |
| --- | --- | --- |
| FGF19+ intestine | 36.7 | 8.2 |
| FGF19− intestine | 39.5 | 0.5 |
| FGF19+ colon | 19.4 | 10.3 |
| FGF19− colon | 15.9 | 3.2 |

Figure 14:
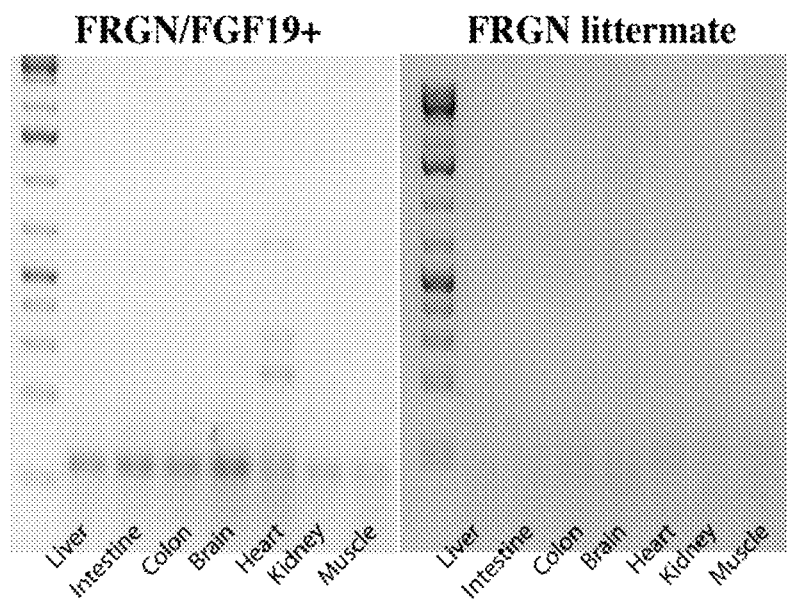
FIG. 14 is an image of a polyacrylamide gel indicating amplified FGF19 in the indicated tissues in FRGN-FGF19 transgenic mice (FRGN/FGF19+) and FRGN littermate controls.
Figure 15:
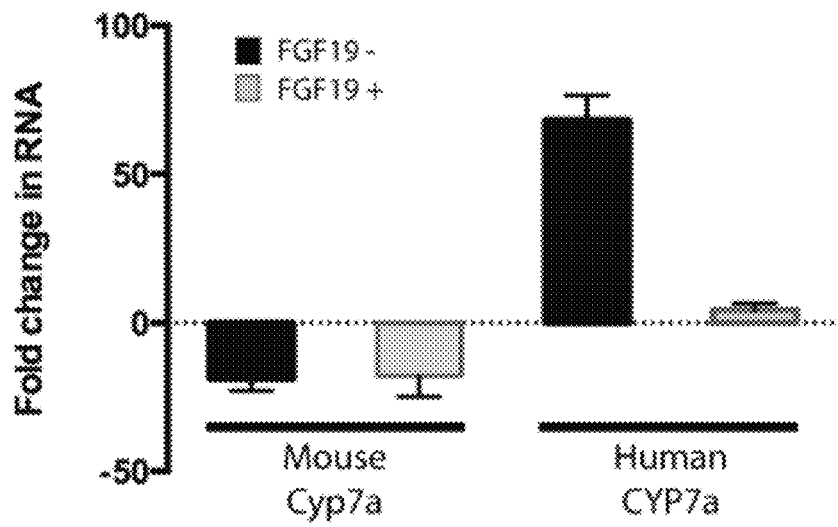
FIG. 15 is a graph of the mRNA expression of mouse Cyp7a and Human CYP7A collected from mice with human-hepatocyte repopulated livers, from either FRGN mice with the FGF19 transgene (grey bars) or their non-FGF19tg FRGN littermates. Expression was measured by quantitative real time PCR, and values normalized to the appropriate housekeeping genes (mouse Gapdh for mouse Cyp7A, and human lamin for human CYP7A). Human CYP7A is appropriately down-regulated in FGF19tg mice with human hepatocyte repopulated livers compared to their non-FGF19tg littermates, where CYP7A is roughly 80-fold higher in expression.
Figure 16:
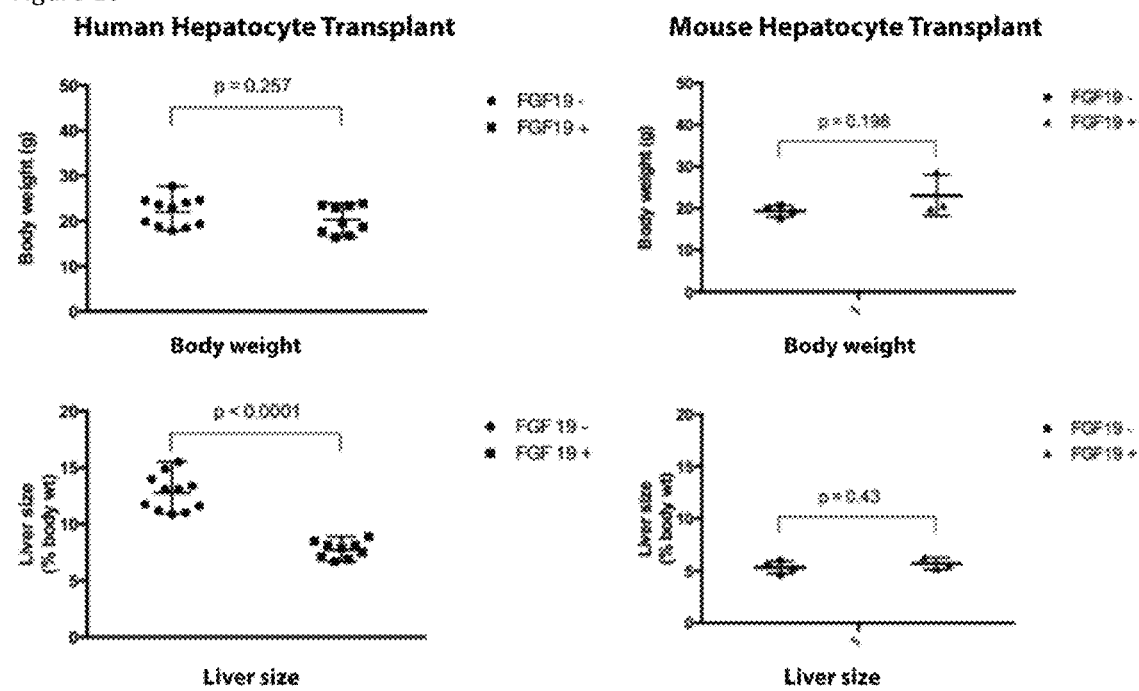
FIG. 16 is a set of four plots showing body weight (top plots) and liver size as percentage of body weight (bottom plots) for mice transplanted with either human or mouse hepatocytes. Mice with human hepatocyte-repopulated livers have markedly enlarged liver sizes, which are significantly normalized in FGF19tg mice. This phenomenon is not seen when mouse hepatocytes are used to repopulate the livers, showing that the phenomenon is specific to miscues in bile acid signaling between human hepatocytes and mouse FGF15.
Figure 17:
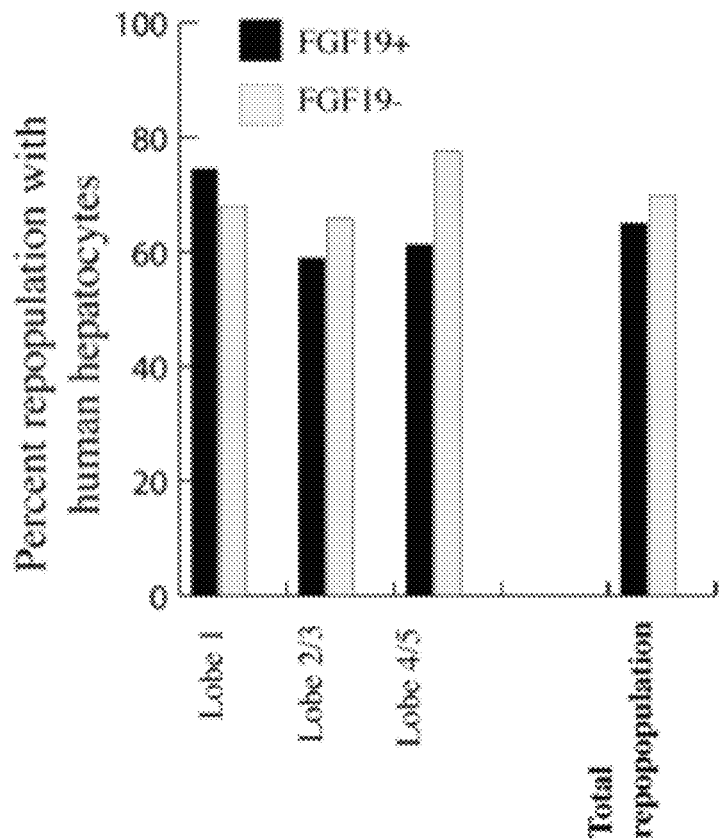
FIG. 17 is a bar graph quantitating the percentage of repopulation of human hepatocytes, FGF19tg mice in gray and the non-FGF19tg littermates in black. The quantitation was done by staining liver section for FAH (only seen in repopulating human liver hepatocytes) and examining the sections histologically with a software analysis program used for morphometric quantitation. This graph shows that repopulation is similar on a percentage basis between FGF19tg and non-FGF19tg mice, despite the overall differences in liver size as noted in FIG. 16.
Figure 18:
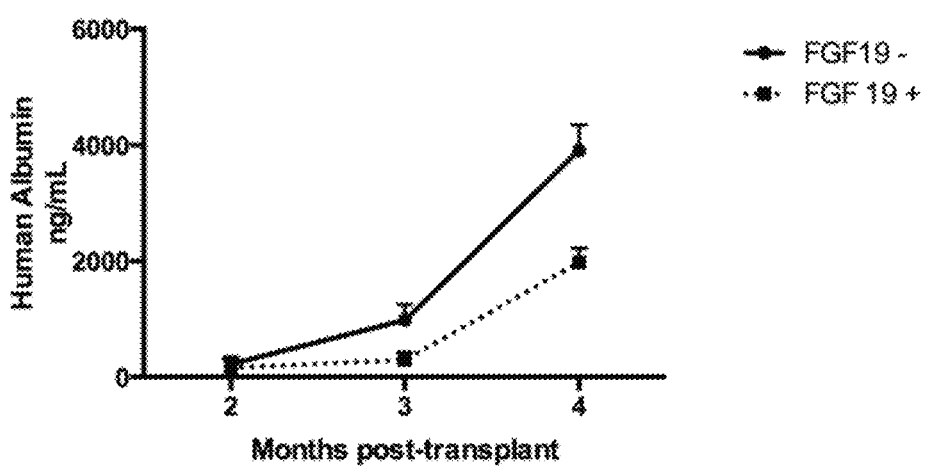
FIG. 18 is a line graph shows serum levels of human albumin measured from the blood of mice undergoing repopulation with human hepatocytes. The human albumin is measured by ELISA assay, and levels roughly correlate with amount of human hepatocytes in the chimeric livers. Note that the general trends of increase over time are similar over time, but the levels are higher in the non-FGF19tg mice, which correlates with smaller overall liver size but similar repopulation percentages as shown in FIGS. 16 and 17.
Figure 19:
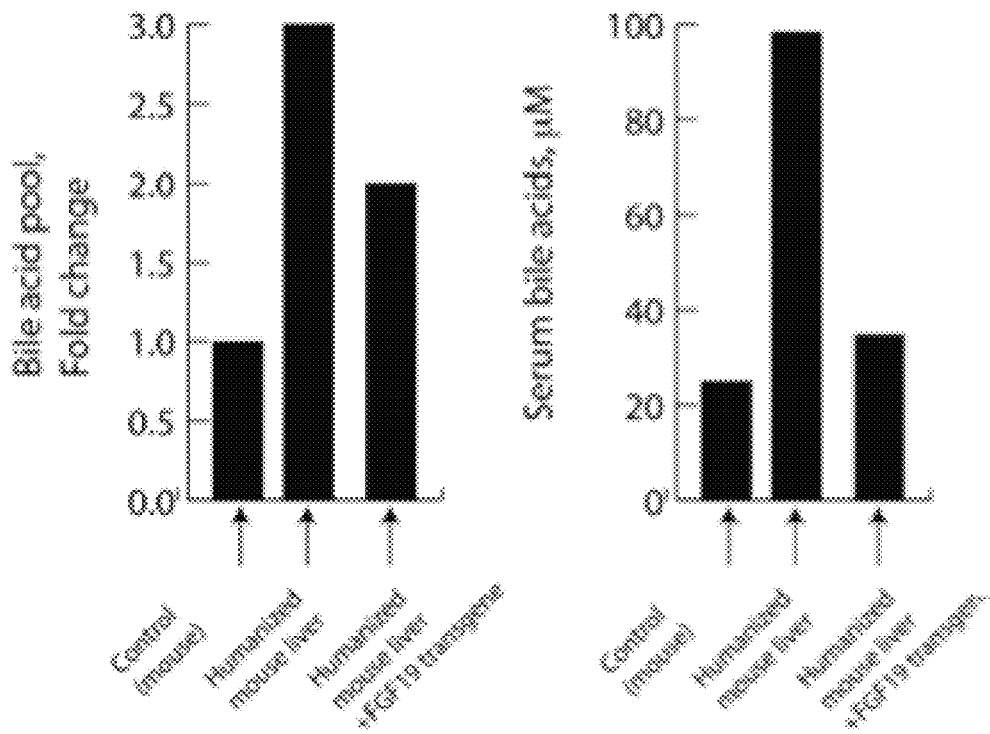
FIG. 19 is a set of three graphs showing the bile acid pools in mice with human (top two graphs) and mouse (bottom graph) hepatocyte transplants and repopulation. Note that in non-FGF19tg human repopulated mice the bile acid pool is markedly larger compared to a normal mouse, while in FGF19tg mice the bile acid pools are diminished (though not completely normalized), and the same phenomenon is seen in the serum bile acids. These changes are not seen when the liver is repopulated with mouse hepatocytes.
Figure 19:
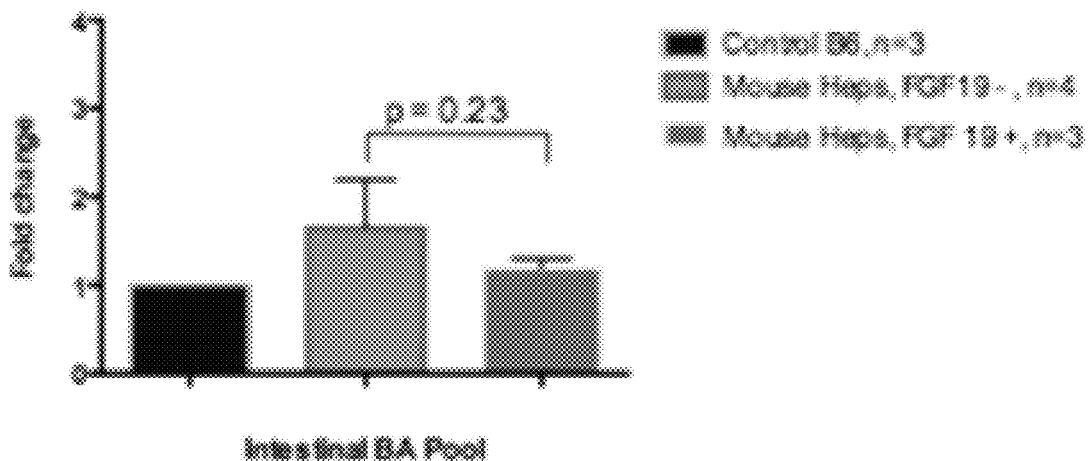

Quantitative PCR for mRNA was performed in several tissues of the FGF19 transgenic mice and compared to their littermates who were FGF19 negative (FIG. 14). These qPCR results show that FGF19 is being produced in many of the tissues in the FGF19 transgenic mouse (most prominently in liver, intestine, colon, with small levels in the brain, and barely detectable levels elsewhere. No detectable FGF19 is seen in the non-transgenic littermates.

To test whether the FGF19 gene introduced into the transgenic mouse is capable of normalizing bile acid production, bile acids (BA) were added exogenously to the mouse via continuous infusion through the portal vein for 24 hours. After 24 hours of BA infusion, mice and controls were sacrificed, and various tissues assayed by qPCR (Tables 5, 6, and 7). These tables show that FGF19 expression is upregulated with administration of BA, as would be expected under normal transcriptional control. While FGF19 was upregulated in the intestine as would be expected, this upregulation was modest; however, FGF19 upregulation in the liver was more marked. The same phenomenon of upregulation in the liver was not seen with FGF15. Table 7 shows that liver Cyp7a1 (rate-limiting enzyme for BA production) is sharply downregulated with BA administration, indicating that FGF19 expression in the transgenic animals is responsive to signals from the liver and therefore would be capable of normalizing bile acid production in a mouse comprising engrafted human hepatocytes.

TABLE 5

Quantitative PCR of FGF19 in NOD/FRG mice (FRGN), NOD/FRG/FGF19 Transgenics (FRGN/FGF19) and NOD/FRG/FGF19 treated with bile acids (FRGN/FGF19 + BA) as described above. Values are normalized to cyclophilin expression by the same formula as in Table 4.

|  | FRGN | FRGN/FGF19 | FRGN/FGF19 + BA |
| --- | --- | --- | --- |
| Liver | 0 | 6.8 | 15.0 |
| Intestine | 0 | 5.8 | 10.1 |
| Colon | 2.7 | 7.1 | 9.4 |

TABLE 6

Quantitative PCR of FGF15 in NOD/FRG mice (FRGN), NOD/FRG/FGF19 Transgenics (FRGN/FGF19) and NOD/FRG/FGF19 treated with bile acids (FRGN/FGF19 + BA) as described above. Values are normalized to cyclophilin expression by the same formula as in Table 4.

|  | FRGN | FRGN/FGF19 | FRGN/FGF19 + BA |
| --- | --- | --- | --- |
| Liver | 4.6 | 5.7 | 6.6 |
| Intestine | 33.9 | 30.4 | 44.4 |
| Colon | 18.1 | 11.0 | 12.1 |

TABLE 7

Quantitative PCR of CYP7a1 in NOD/FRG mice (FRGN), NOD/FRG/FGF19 Transgenics (FRGN/FGF19) and NOD/FRG/FGF19 treated with bile acids (FRGN/FGF19 + BA) as described above. Values are normalized to cyclophilin expression by the same formula as in Table 4.

|  | FRGN | FRGN/FGF19 | FRGN/FGF19 + BA |
| --- | --- | --- | --- |
| Liver | 33.6 | 28.5 | 8.6 |

Example 8

Detection of Human FGF19 Regulatory Sequences

An FGF19 transgenic mouse may comprise an FGF19 promoter and/or one or more additional FGF19 regulatory sequences. Such regulatory sequences may comprise one or more FGF19 promoters, enhancers, silencers, transcription factor binding sites, or any other sequence that can modulate the expression of FGF19 when the sequence is present. One example of such a mouse is a mouse that comprises an approximately 150 kb chromosomal region comprising FGF19, such as BAC RP11-266K14. However, other examples of such FGF19 transgenic mice include mice that comprise FGF19 coding sequence (including an FGF19 cDNA) along with sequences determined to act as an FGF19 regulatory sequence.

Such regulatory sequences may be identified by cloning subsequences from BAC RP11-266K14, from human chromosome 11, or from other parts of the human genome into a reporter construct comprising a reporter construct. The reporter construct may be any gene, the expression of which yields a result that may be detected by the aided or unaided human eye, a fluorescent detector, a camera, or any other sensor configured to detect the presence or absence of the reporter construct. Cloned subsequences that cause the expression of the reporter construct in an appropriate cell line such as a small intestine cell line, colon cell line, or potentially hepatocyte cell line would likely be FGF19 promoter sequences. Cloned subsequences that cause greater expression of the reporter construct than in the presence of the promoter alone would likely be FGF19 enhancer sequences, and cloned subsequences that result in less expression of the reporter construct than in the presence of the promoter alone would likely be FGF19 suppressor sequences. One of skill in the art, especially in light of this disclosure, would readily be able to achieve the proper number and location of FGF19 regulatory sequences to generate an FGF19 transgenic mouse with normalized bile acid production.

Example 9

Correction of Abnormal Bile Acid Signaling and Liver Size in Mice with Humanized livers by Use of the FGF19tg Mouse As stated above, repopulation of mouse livers with human hepatocytes results in enlarged livers, a phenomenon which is not restricted to the FAH model. As we have shown, the bile acid signaling machinery is perturbed in human-repopulated mouse livers, resulting in an increase in the size of the total bile acid pool as a result of significant up-regulation of the key regulatory bile acid synthetic enzyme, CYP7A, in the human (but not mouse) hepatocytes in the chimeric-livers. This phenomenon is a result of the human hepatocytes inability to recognize the key negative feedback signal originating in the intestine, FGF15, which is the mouse ortholog of human FGF19. Administration of exogenous recombinant FGF19 inhibits the dysregulated CYP7A as expected and shown in our paper. Here we show that the FRGN-FGF19tg mice also allow efficient repopulation of the liver with human hepatocytes, but that the introduction of the FGF19tg corrects the abnormally high CYP7A in the human hepatocytes, decreases the abnormally enlarged bile acid pool towards normal, and decreases the liver size of chimeric livers towards normal.

In view of the many possible embodiments to which the principles of the present disclosure may be applied, it should be recognized that the illustrated embodiments are only preferred examples and should not be taken as limiting the scope of the present disclosure. Rather, the scope of the present disclosure is defined by the following claims. We therefore claim all that comes within the scope and spirit of these claims.

The invention claimed is:

1. A genetically modified mouse whose genome is homozygous for disruptions in at least the Fah and Rag2 genes such that said disruptions result in loss of expression of functional Fah and Rag2 proteins, wherein said mouse also comprises a genetic alteration that results in the insertion of a nucleic acid expressing FGF19, and wherein the genetically modified mouse exhibits normalized bile acid production.

2. The transgenic mouse of claim 1, wherein the host animal is of a genotype selected from the group consisting of $Fah^{-/-}/Rag2^{-/-}/FGF19$ tg, and $NOD/Fah^{-/-}/Rag2^{-/-}/FGF19$tg.

* * * * *

UNITED STATES PATENT AND TRADEMARK OFFICE
CERTIFICATE OF CORRECTION

PATENT NO. : 9,566,315 B2  
APPLICATION NO. : 14/529011  
DATED : February 14, 2017  
INVENTOR(S) : Markus Grompe and Willscott Naugler Page 1 of 1

It is certified that error appears in the above-identified patent and that said Letters Patent is hereby corrected as shown below:

In the Specification

At Column 1, Lines 9-12, under the heading ACKNOWLEDGEMENT OF GOVERNMENT SUPPORT, please delete the following:
"This invention was made with United States government support under the terms of grant number R01DK05192 awarded by the National Institutes of Health. The United States government has certain rights in the invention."

And replace it with the following:
-- This invention was made with government support under EY009275 and MH071625 awarded by the National Institutes of Health. The government has certain rights in the invention. --

Signed and Sealed this  
Ninth Day of July, 2019

Andrei Iancu  
*Director of the United States Patent and Trademark Office*

UNITED STATES PATENT AND TRADEMARK OFFICE
CERTIFICATE OF CORRECTION

| | | |
|---|---|---|
| PATENT NO. | : 9,566,315 B2 | Page 1 of 1 |
| APPLICATION NO. | : 14/529011 | |
| DATED | : February 14, 2017 | |
| INVENTOR(S) | : Markus Grompe and Willscott Naugler | |

It is certified that error appears in the above-identified patent and that said Letters Patent is hereby corrected as shown below:

In the Specification

Replace the paragraph at Column 1, Lines 9-12 with the following text:
"This invention was made with government support under DK051592 awarded by the National Institutes of Health. The government has certain rights in the invention."

Signed and Sealed this
First Day of December, 2020

Andrei Iancu
*Director of the United States Patent and Trademark Office*